United States Patent
Yeh

(10) Patent No.: US 10,557,163 B2
(45) Date of Patent: Feb. 11, 2020

(54) BACTERIAL DETECTION CARTRIDGE

(71) Applicant: BECTON DICKINSON AND COMPANY, Franklin Lakes, NJ (US)

(72) Inventor: Ming-Hsiung Yeh, New Freedom, PA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 191 days.

(21) Appl. No.: 15/881,246

(22) Filed: Jan. 26, 2018

(65) Prior Publication Data

US 2018/0148760 A1  May 31, 2018

Related U.S. Application Data

(62) Division of application No. 14/775,100, filed as application No. PCT/US2013/030155 on Mar. 11, 2013, now Pat. No. 9,909,162.

(51) Int. Cl.
| | |
|---|---|
| *C12Q 1/04* | (2006.01) |
| *C12M 1/34* | (2006.01) |
| *G01N 33/50* | (2006.01) |
| *B01L 3/00* | (2006.01) |

(52) U.S. Cl.
CPC ............ *C12Q 1/04* (2013.01); *B01L 3/50853* (2013.01); *G01N 33/50* (2013.01);
(Continued)

(58) Field of Classification Search
CPC ...... C12Q 1/04; C12M 41/36; B01L 3/50853; B01L 2200/025; B01L 2200/0689;
(Continued)

(56) References Cited

U.S. PATENT DOCUMENTS

| | | |
|---|---|---|
| 4,070,248 A | 1/1978 | Schmidt |
| 4,145,304 A | 3/1979 | Melnick et al. |
| | (Continued) | |

FOREIGN PATENT DOCUMENTS

| | | |
|---|---|---|
| CN | 1140763 A | 1/1997 |
| CN | 1154477 A | 7/1997 |
| | (Continued) | |

OTHER PUBLICATIONS

European Office Communication for Application No. 13713611.5 dated May 3, 2017.
(Continued)

*Primary Examiner* — Michael L Hobbs
(74) *Attorney, Agent, or Firm* — Botos Churchill IP Law LLP

(57) ABSTRACT

Described herein are methods and apparatus for rapid detection of microorganisms in biological samples (e.g. blood) for analysis to determine the presence or absence of infectious microorganisms in the samples. The apparatus includes a cartridge with a lid and a tray, a mechanism for isolating a bulk sample into multiple smaller samples, and a sensor disposed on the tray to determine the presence or absence of microorganisms. The cartridge lid includes projections that, in a first position, allow for sample to distribute evenly in the cartridge tray and, in a second position, isolate the sample into multiple smaller volume samples. The apparatus and method shorten the time-to-detection of a microorganism in a sample and reduce the steps required from sample collection to microorganism detection.

7 Claims, 27 Drawing Sheets

(52) U.S. Cl.
CPC . *B01L 2200/025* (2013.01); *B01L 2200/0689* (2013.01); *B01L 2300/069* (2013.01); *B01L 2300/0636* (2013.01); *B01L 2400/0694* (2013.01); *C12M 41/36* (2013.01); *G01N 2800/26* (2013.01)

(58) Field of Classification Search
CPC ....... B01L 2300/069; B01L 2300/0636; B01L 2400/0694; G01N 33/50
See application file for complete search history.

(56) References Cited

U.S. PATENT DOCUMENTS

| | | | |
|---|---|---|---|
| 5,182,082 | A | 1/1993 | Monthony et al. |
| 5,624,814 | A | 4/1997 | Waters et al. |
| 5,891,739 | A | 4/1999 | Berndt |
| 2002/0098125 | A1 | 7/2002 | Roberts et al. |
| 2012/0231533 | A1* | 9/2012 | Holl ................ C12M 23/12 435/287.9 |

FOREIGN PATENT DOCUMENTS

| | | | |
|---|---|---|---|
| CN | 201313888 Y | 9/2009 | |
| CN | 102495051 A | 6/2012 | |
| EP | 0751216 A1 | 1/1997 | |
| EP | 0751393 A2 * | 1/1997 | ............ B01L 3/5085 |
| EP | 0751393 A2 | 1/1997 | |
| JP | H0923875 | 1/1997 | |
| WO | 9955827 A1 | 11/1999 | |
| WO | 2010062654 A2 | 6/2010 | |

OTHER PUBLICATIONS

International Search Report and Written Opinion for Application No. PCT/US2013/030155 dated Feb. 11, 2014.
Partial International Search Report for Application No. PCT/US2013/030155 dated Oct. 28, 2013.
Search Report from CN2013800764926 Office Action dated Dec. 2, 2016.

* cited by examiner

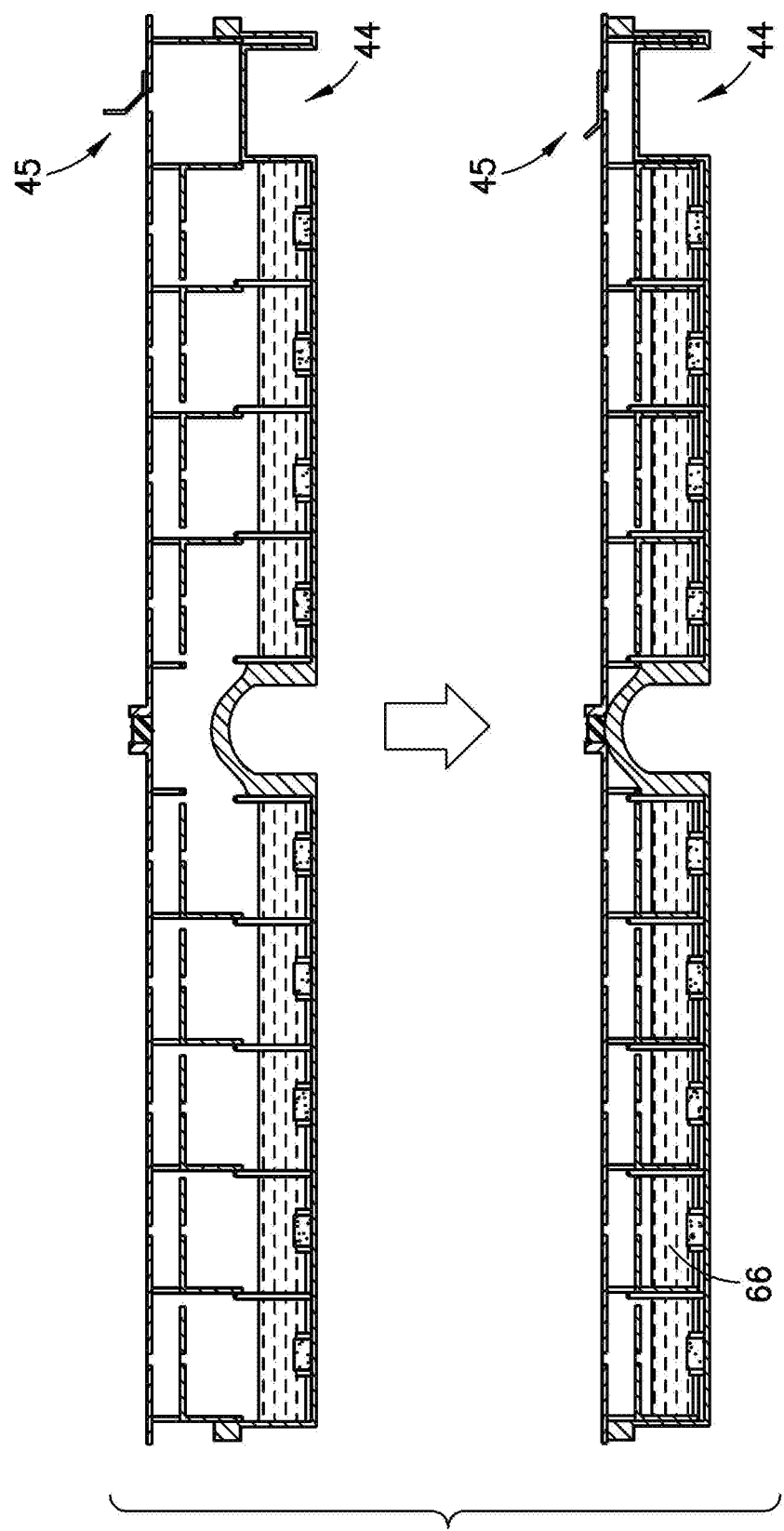

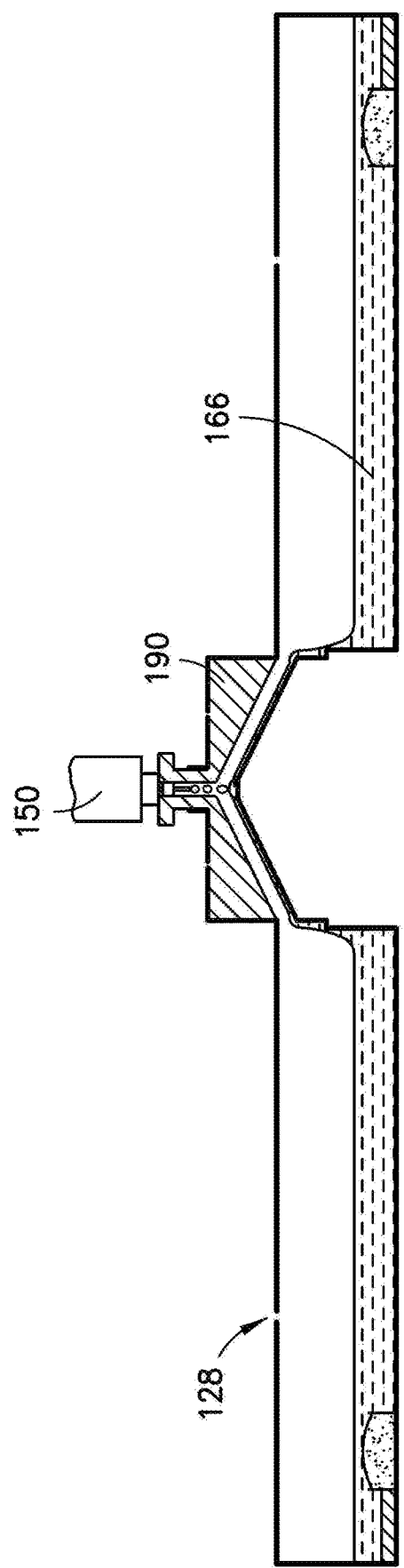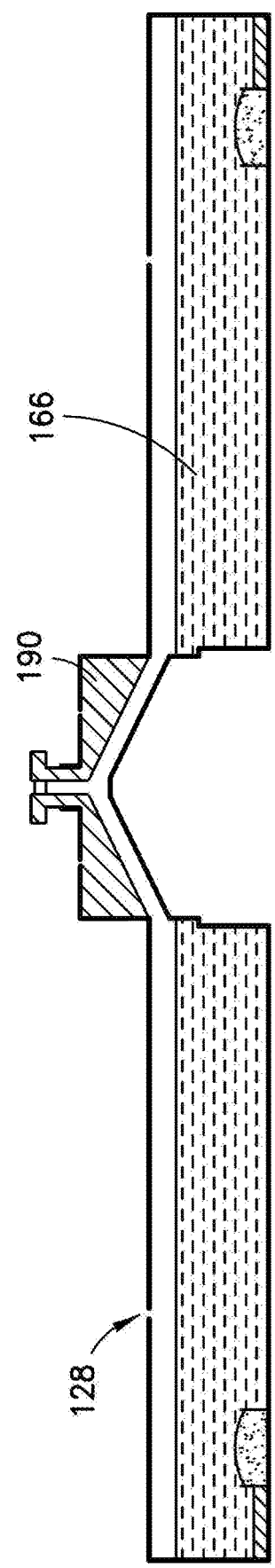
FIG. 25A
FIG. 25B

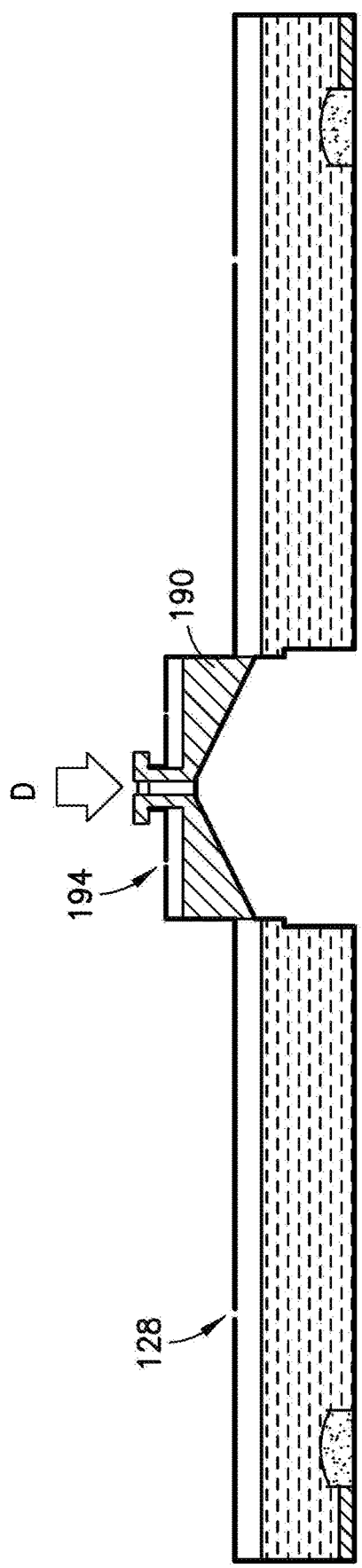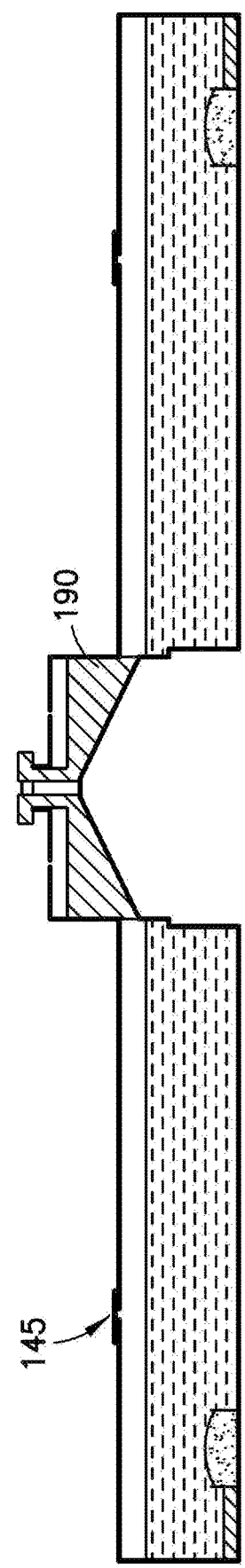

BACTERIAL DETECTION CARTRIDGE

CROSS-REFERENCE TO RELATED APPLICATIONS

This application is a divisional of U.S. application Ser. No. 14/775,100, now U.S. Pat. No. 9,909,462, filed on Sep. 11, 2015, which is a national phase entry under 35 U.S.C. § 371 of International Application No. PCT/US2013/030155, filed on Mar. 11, 2013, published in English, all of which are incorporated herein by reference.

BACKGROUND OF THE INVENTION

Sepsis is a significant healthcare issue due to its high frequency of occurrence and high mortality rate in hospitals. Sepsis is characterized by a whole-body inflammatory state, called a systemic inflammatory response (SIRS), and by the presence of a known or suspected infection. The immune system may cause this inflammatory response as a consequence of microbes in the blood, urine, lungs, skin, or other tissues, for example. One of the leading causes of sepsis is a bloodstream infection (BSI). BSI is most commonly diagnosed by a blood culture, in which a sample of blood is incubated with a medium in an atmosphere controlled to promote bacterial growth.

Current automated blood culture systems can take 12-48 hours to detect the presence of infectious microorganisms in blood and can take up to 5 days to rule out the presence of any infectious microorganisms. It can take up to another 12-48 hours to identify the infectious microorganisms by sub-culturing the positive blood culture and performing identification and antimicrobial susceptibility tests. These results can be too late to alter the treatment course and result in the death of the patient.

One approach to faster bacterial time to detection ("TTD") is dividing the sample liquid together with growth media into a large number of smaller volume samples that are contained in closed small volume compartments (see U.S. Pat. No. 5,770,440 and 5,891,739 to Berndt, the entire contents of which are both hereby incorporated by reference herein). The added steps required to segregate the blood/media sample into smaller volume samples can be difficult and time consuming. Additionally, designing a product to address this increased workflow can be limited by considerations of manufacturability and cost. Consequently, a small-volume compartment BSI product design that is easy to manufacture, cost effective, less time-consuming to use and reduces TTD in a clinical sample is desired.

BRIEF SUMMARY OF THE INVENTION

Described herein are methods and apparatus for rapid detection of microorganisms in biological samples (e.g. blood) for analysis to determine the presence or absence of infectious microorganisms in the samples. The apparatus includes a cartridge with a lid and a tray, a mechanism for isolating a bulk sample into multiple smaller samples, and a sensor disposed on the tray to determine the presence or absence of microorganisms.

According to the methods described herein, the cartridge lid is assembled onto the cartridge tray in a first position, the sample introduced into the cartridge tray and allowed to distribute across the volume of the cartridge tray, and the cartridge lid is moved into a second position creating a plurality of compartments isolating the bulk sample into multiple samples of a smaller volume. The method and apparatus allow for, inter alia, a reduced time-to-detection for microorganisms in a biological sample and obviates the need to manually dispense a sample into individual compartments of a detection device.

BRIEF DESCRIPTION OF THE DRAWINGS

FIG. 15 shows a side view of the cartridge lid and tray transitioning from a first position to a second position.

FIGS. 25A-B show a sectional view of the cartridge of FIG. 23 during and after sample introduction, respectively.

FIG. 26A shows a sectional view of the filled cartridge of FIG. 25B in a second position.

FIG. 26B shows the filled cartridge of FIG. 26A after vents are sealed.

DETAILED DESCRIPTION

Figure 2:
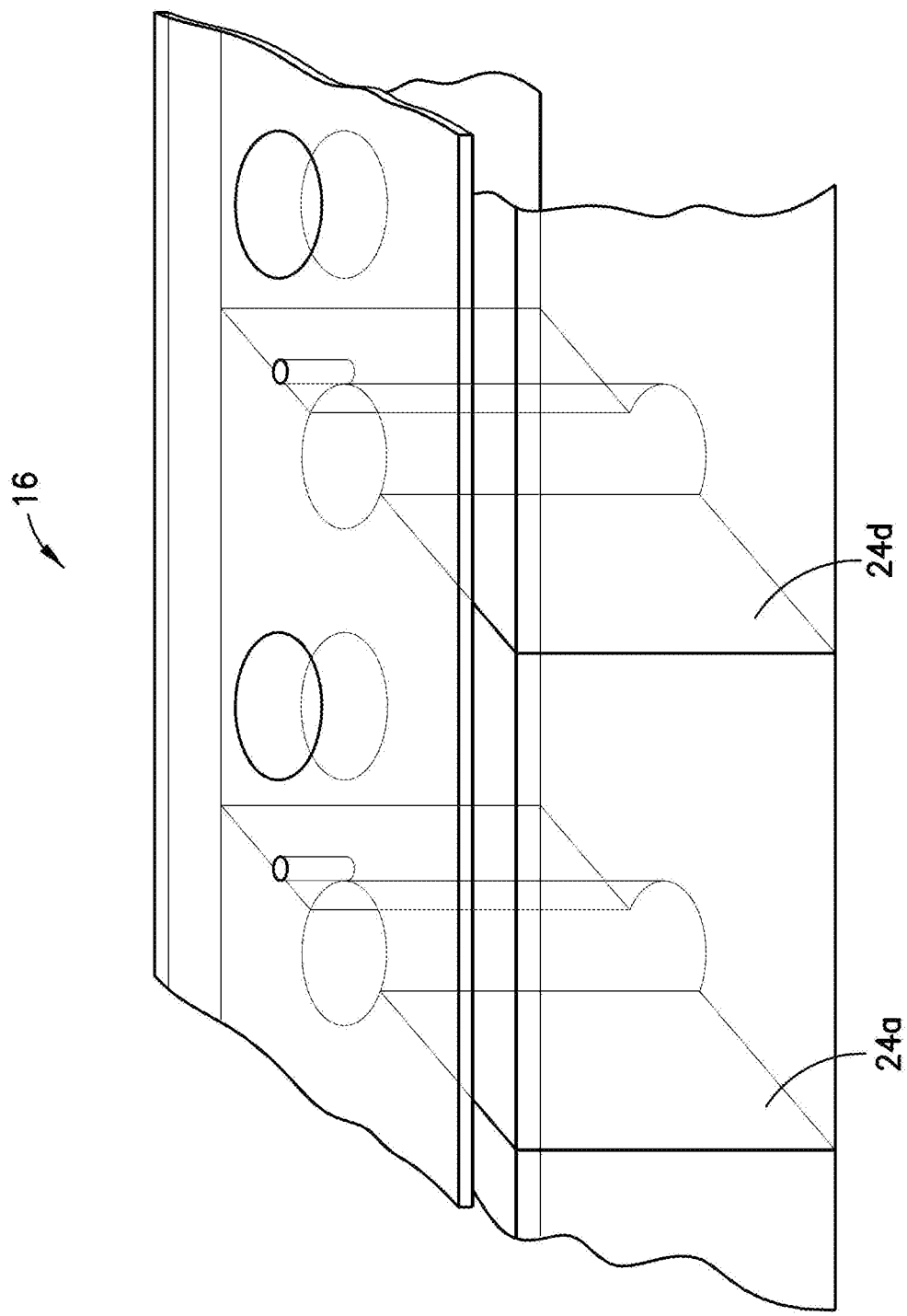
FIG. 2 shows a perspective view of the top and bottom lid portions of FIG. 1 assembled together.
Figure 3:
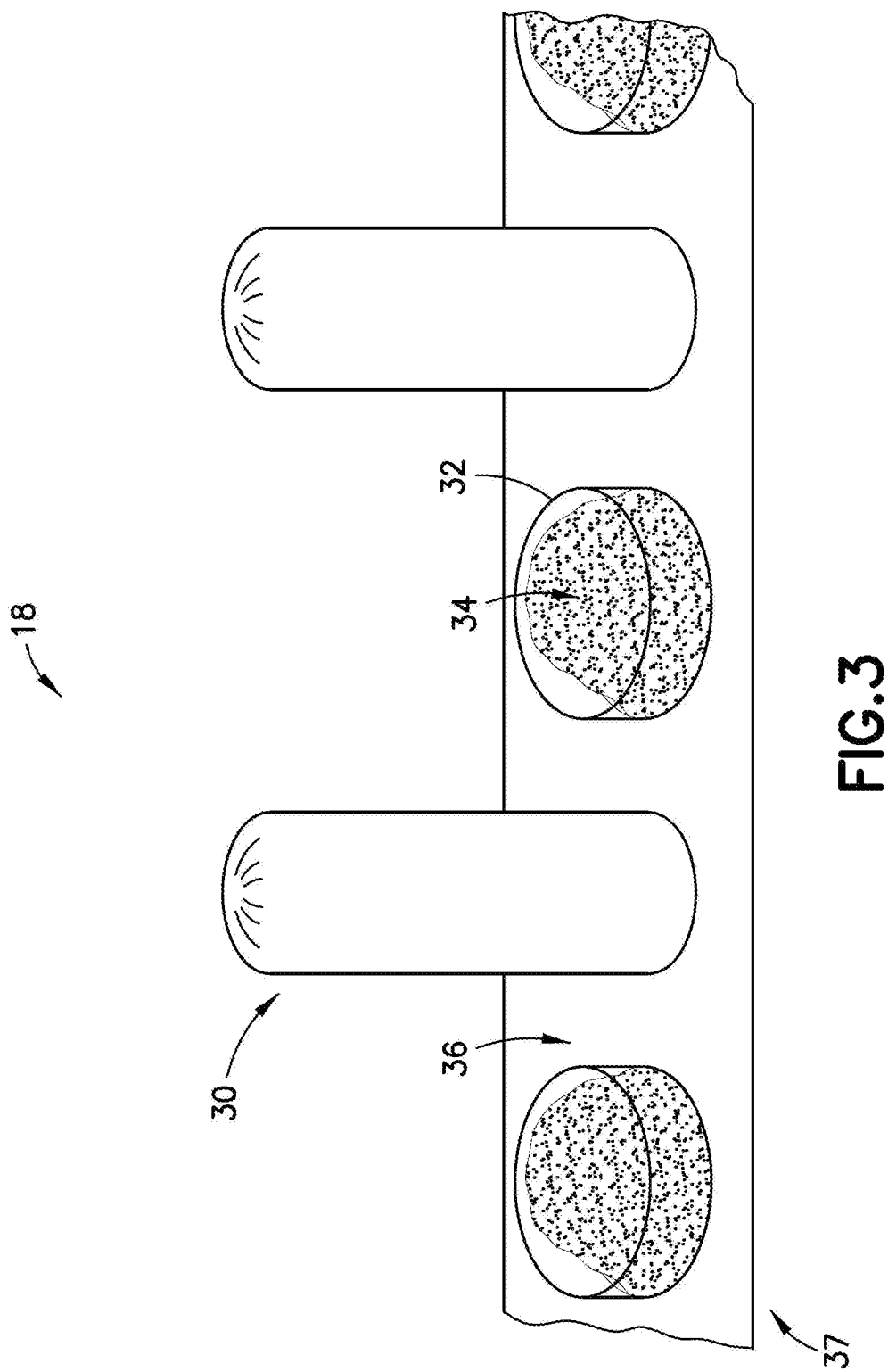
FIG. 3 shows a perspective view of a portion of a cartridge tray.
Figure 4:
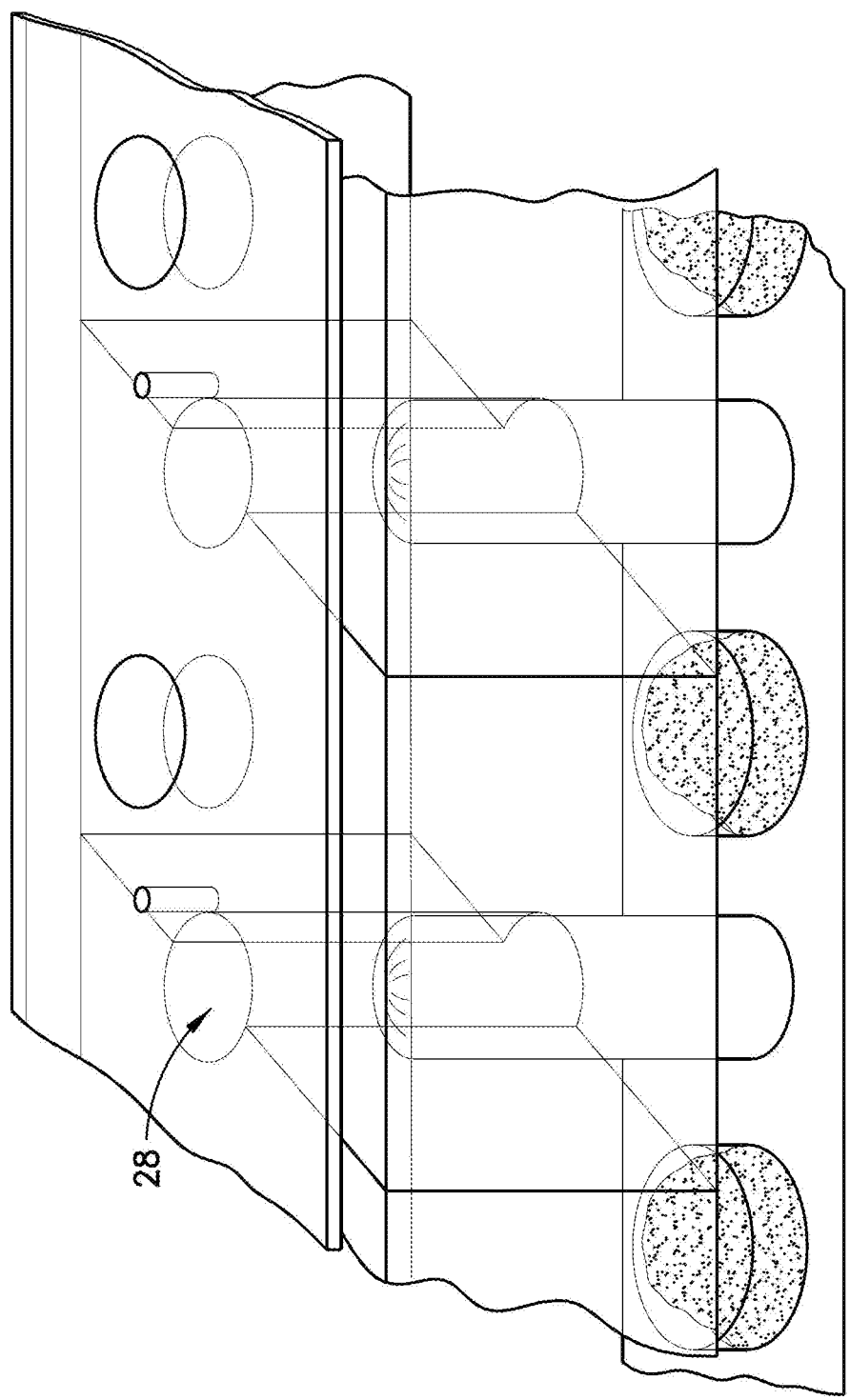
FIG. 4 shows a perspective view of the cartridge lid assembly of FIG. 2 mated to the cartridge tray of FIG. 3 in a first position.

Referring generally to FIGS. 1-5, a bacterial detection cartridge 10 according to an embodiment of the invention generally includes a cartridge lid assembly 16 and a cartridge tray 18. The cartridge lid assembly 16 is composed of a top lid portion 12 and a bottom lid portion 14 which can be made separately, for example via injection-molding, and snapped together to form the cartridge lid assembly 16. The cartridge lid assembly 16 is then positioned onto the cartridge tray 18 in an elevated first position (FIG. 4). The cartridge lid assembly 16 can then be pushed down to lock the bacterial detection cartridge 10 into a second position (FIG. 5) after sample 66 (FIG. 16) has been introduced into the cartridge tray 18 through a sample injection port 20 (FIG. 1) defined in top lid portion 12. In one embodiment, the bacterial detection cartridge 10 containing the sample 66 is made ready for sample incubation. All compartments 24 are configured to allow for sample removal when the tray is in the second position. Therefore, any compartment 24 with sample 66 for which a positive detection result was obtained can be accessed for sample removal for further analyses.

Figure 1:
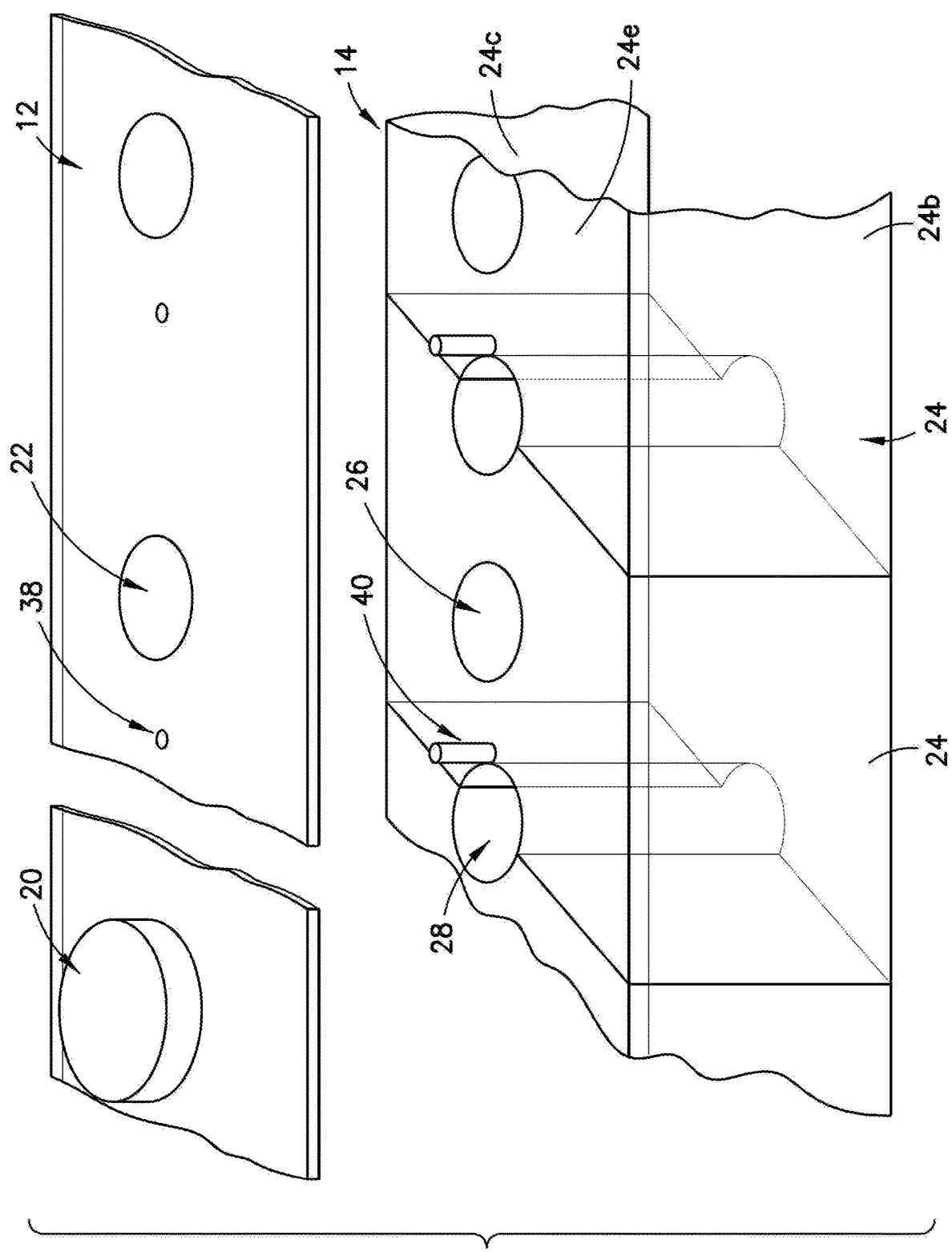
FIG. 1 shows a perspective view of one embodiment of a portion of a top and bottom lid portion of a cartridge lid.

Referring generally to FIGS. 1-2, the cartridge lid assembly 16 includes a top lid portion 12 and a bottom lid portion 14. The top lid portion 12 includes multiple top lid access apertures 22 positioned near the center of each compartment 24 of the bottom lid portion 14. The top lid access apertures 22 allow a pipette, syringe or other device to access the sample 66 within a selected compartment 24. The top lid access apertures 22 are integrated into the top lid 12 as thin circular areas. A sample injection port 20 is formed in the top lid portion 12 to allow a sample 66 to be introduced into the cartridge tray 18. The port is configured to allow sample introduction into the lid assembly via a syringe or other sample introduction device. A separate re-sealable pressure escaping outlet 42 is also built onto the top lid portion 12 (shown in FIGS. 6-12).

The bottom lid portion 14 defines the compartments 24 in cooperation with the cartridge tray 18. Specifically, each compartment 24 is defined by four downward projecting side-wall portions 24a-d in the bottom lid portion 14, the top wall 24e of the bottom lid portion 14, and the cartridge tray 18. In other words, the bottom lid defines a grid of compartments 24 except for the bottom surface of the compartments, which is defined by the cartridge tray 18. The bottom lid portion 14 also includes multiple bottom lid access apertures 26 positioned in the illustrated embodiment near the center of each compartment 24 and aligned with a corresponding top lid aperture 22. The alignment of the top lid access apertures 22 with the bottom lid access apertures 26 permit an access device, such as a pipette or syringe, to penetrate through both the top lid portion 12 and bottom lid portion 14 to access the compartment 24 underneath. Also included on the bottom lid portion 14 are vents 28 for each compartment 24. The vents 28 align with the seal rods 30 on the cartridge tray 18.

The top lid access apertures 22 can be covered with a pressure sensitive adhesive foil 72 (shown in FIG. 18) to isolate the interior of the bacterial detection cartridge 10 from the environment. In use, after an access device penetrates the top and bottom lid portions 12, 14 to access the compartment 24, the top lid access apertures 22 may be re-sealed, for example with an additional layer of pressure sensitive adhesive foil 72, to again isolate the interior of the cartridge 10 from the environment to provide for safe handling, including disposal and/or autoclaving. In addition to reducing chances of contamination, providing a seal keeps sample components within the compartment 24. For example, without a seal, $CO_2$ could escape from the compartment 24, causing the sensor 36 (described below) to report inaccurate results of bacterial metabolism. Similarly, the bottom lid access apertures 26 may initially be sealed by a material, such as a pressure sensitive adhesive foil (not illustrated). A seal on the bottom lid access apertures 26 isolates the contents of a particular compartment 24 from the headspace between the top lid portion 12 and bottom lid portion 14 when the cartridge lid assembly 16 is in the second position, described more fully below.

Figure 5:
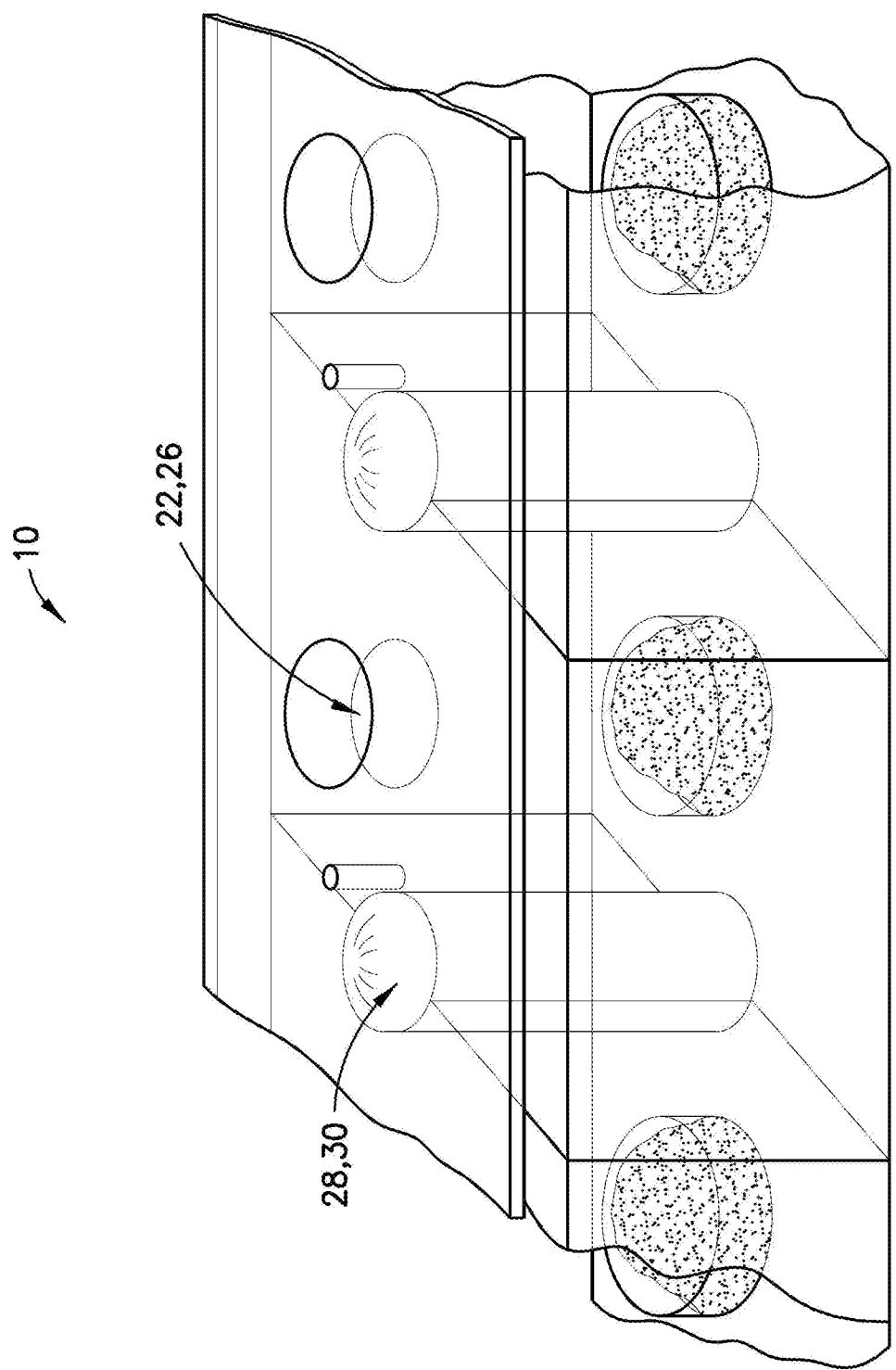
FIG. 5 shows a perspective view of the cartridge lid assembly of FIG. 2 mated to the cartridge tray of FIG. 3 in a second position.

Referring generally to FIGS. 3-5, the cartridge tray 18 is a tray with seal rods 30 and an interior open vessel 32 built on the surface. The vessel 32 is configured to receive reagents such as resin gel pellets 34. The seal rods 30 function to guide the cartridge lid assembly 16 on to the cartridge tray 18, and serve to seal the vents 28 of the compartments 24 when the cartridge lid assembly 16 is moved from the first position to the second position. In one embodiment, the vessel is a raised rim on the surface of the cartridge tray 18. In other embodiments, the resin gel pellets 34 can be applied directly to the cartridge tray without the use of vessels 32. The exact location and the number of the vessels 32 and seal rods 30 are determined by the arrangement of the compartments 24 on the bottom lid portion 14 and is largely a matter of design choice. The cartridge tray 18, top lid portion 12, and bottom lid portion 14 can be made of various materials, such as clear polypropylene or similar optically clear plastic resins such as, but not limited to, polycarbonate, cyclic olefin polymer, and polystyrene. Although it is preferred that the top lid portion 12 and bottom lid portion 14 are a transparent material, other non-transparent materials are contemplated for use in the assembly described herein.

In one embodiment, the cartridge tray 18 is preloaded with biosensor coating 36 on the bottom surface 37 outside the area of the interior open vessels 32. Although a biosensor coating 36 is preferred for the sensor, other sensors known in the art can be used without deviating from the scope of the invention. The sensor 36 can detect, for example, $O_2$ and/or $CO_2$ changes collectively or independently (see U.S. Pat. No. 6,989,246 to Yeh, the entire contents of which are hereby incorporated by reference herein). Antimicrobial adsorption resin gel pellets 34 are dispensed inside the interior open vessels 32. The resin gel pellet is made of, for example, antimicrobial adsorption resins mixed with water-soluble materials for ease of dispensing and resin release capability in aqueous environment. Such resins are known in the art. For example, U.S. Pat. No. 5,624,814 to Waters et al. describes resins added to culture media to isolate microorganisms from substances that have the potential to inhibit the growth of the microorganisms. Other references that contemplate combining a resin with a biological sample to remove growth inhibitors from a biological sample suspected of containing a target microorganism include U.S. Pat. Nos. 4,145,304 and 4,174,277, both to Melnick et al. The entire contents of these references are each hereby incorporated by reference herein.

Figure 6:
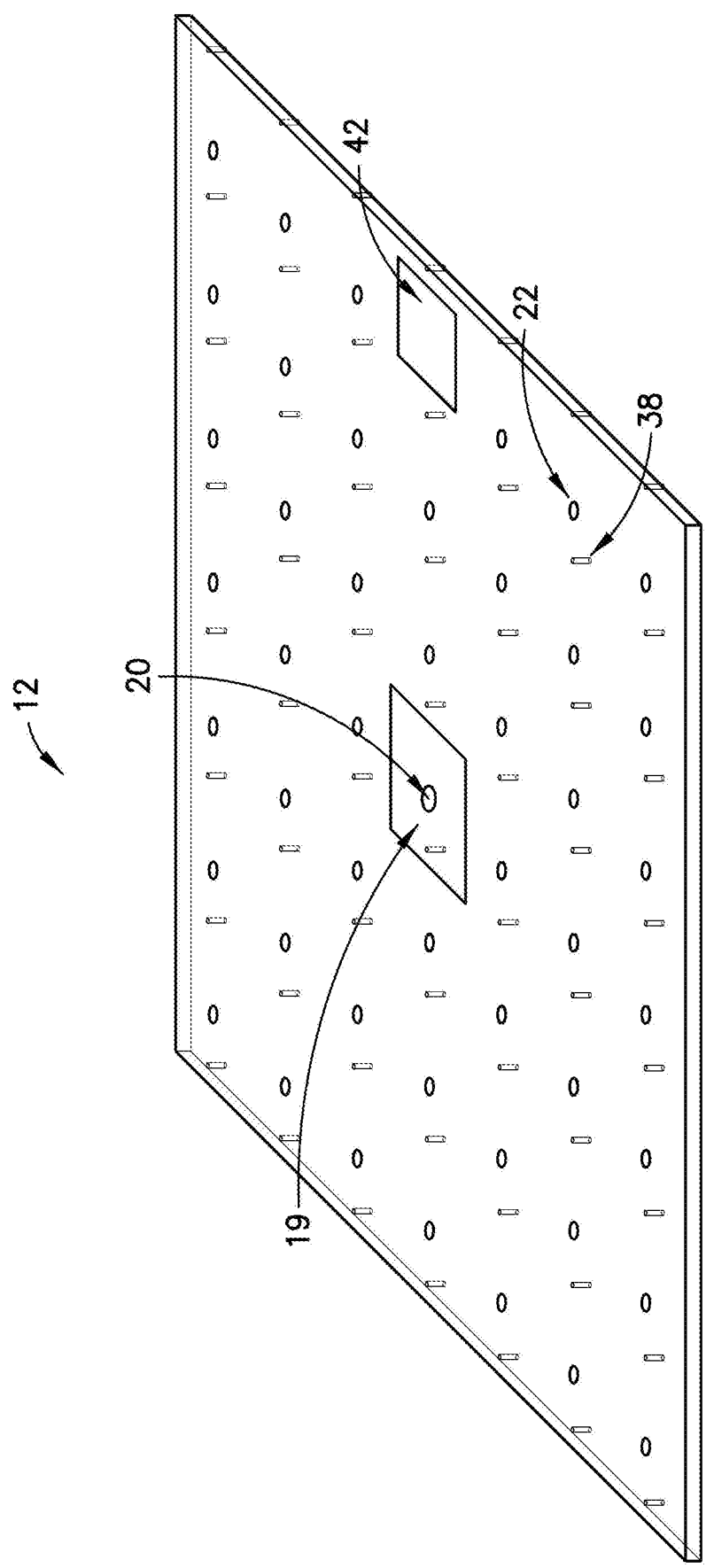
FIG. 6 shows a perspective view of the entire top portion of the cartridge lid shown in FIG. 1.
Figure 7:
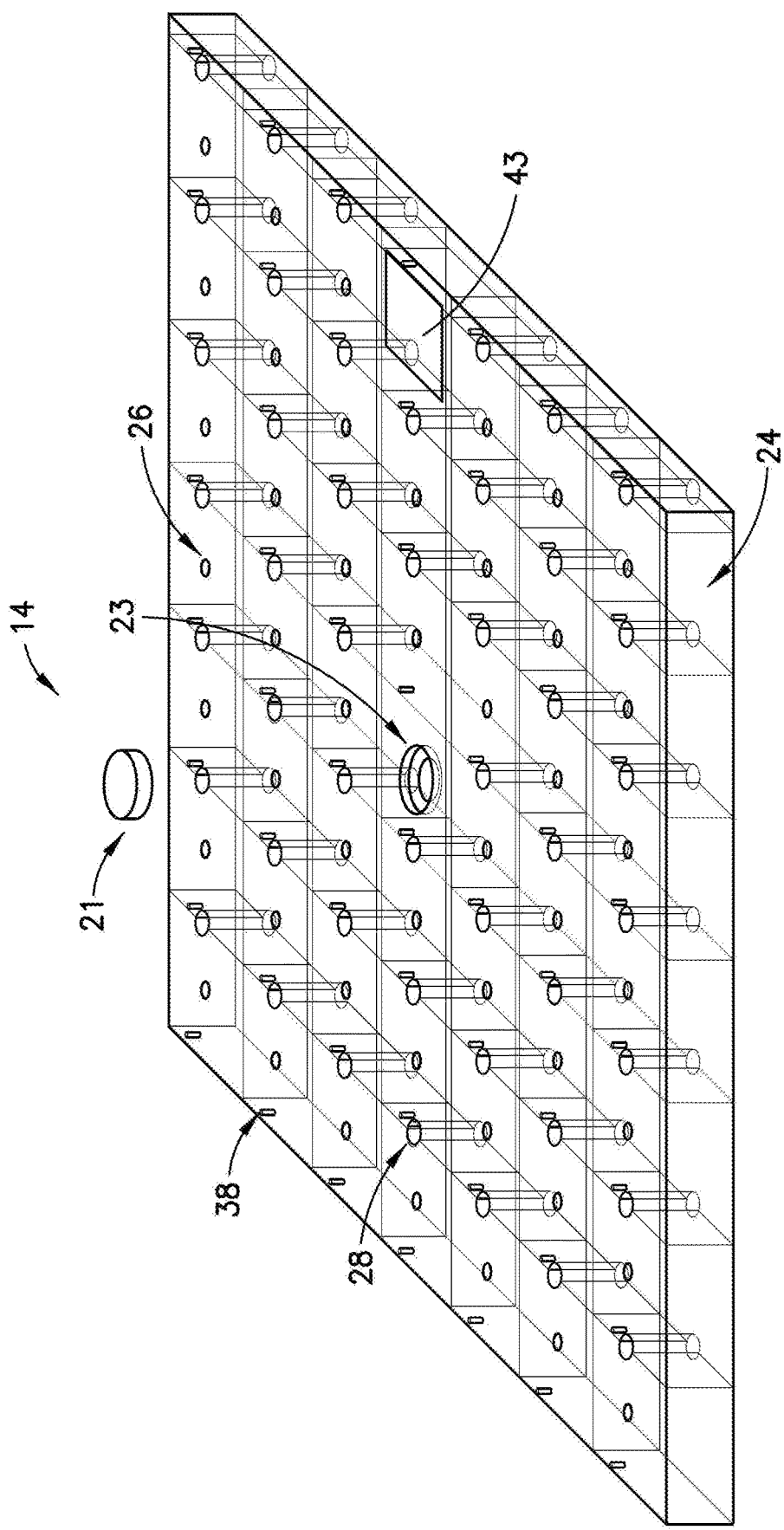
FIG. 7 shows a perspective view of the entire bottom portion of the cartridge lid shown in FIG. 1.
Figure 8:
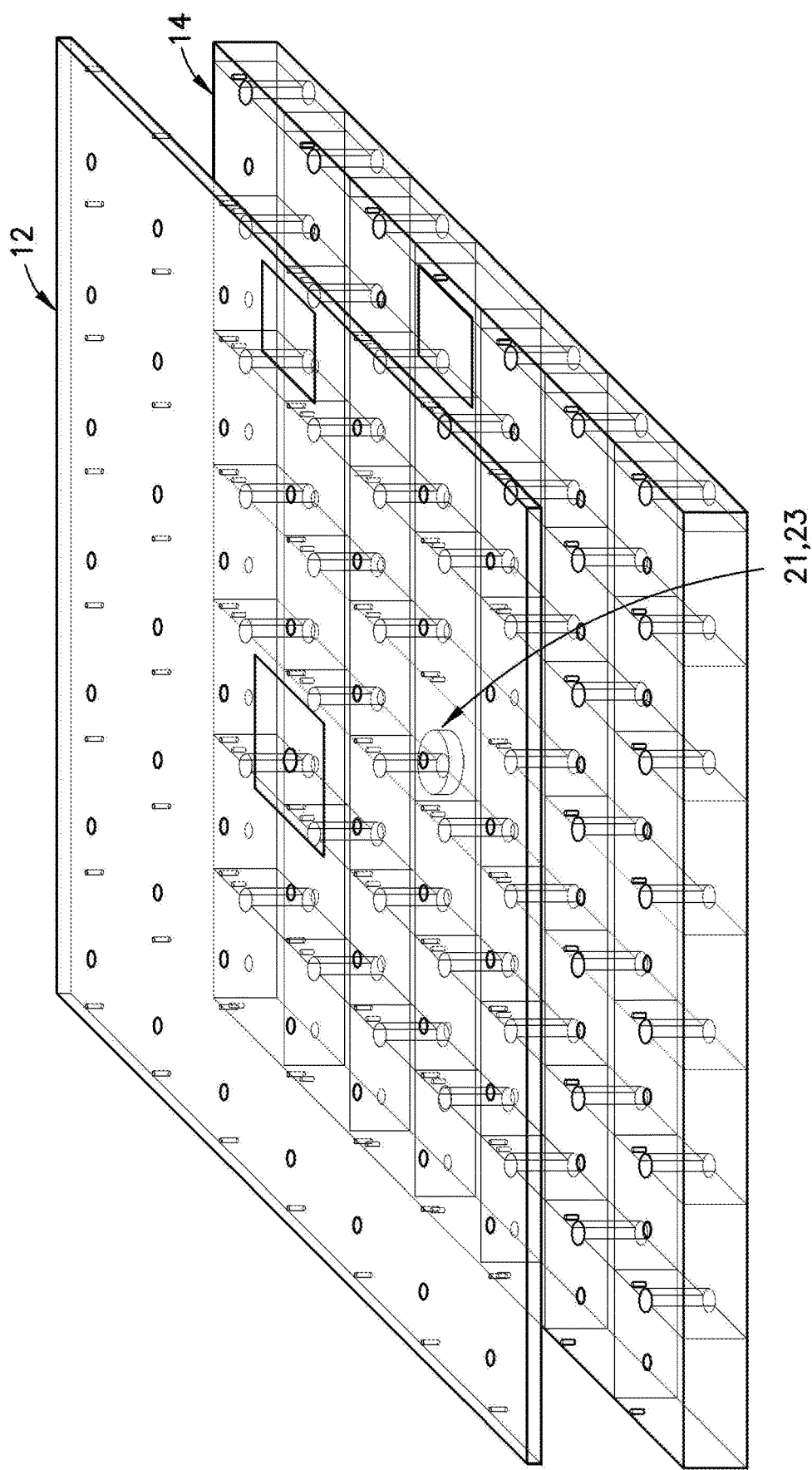
FIG. 8 shows a perspective phantom view of the top and bottom portions of the cartridge lid shown in FIGS. 6 and 7 prior to assembly.
Figure 9:
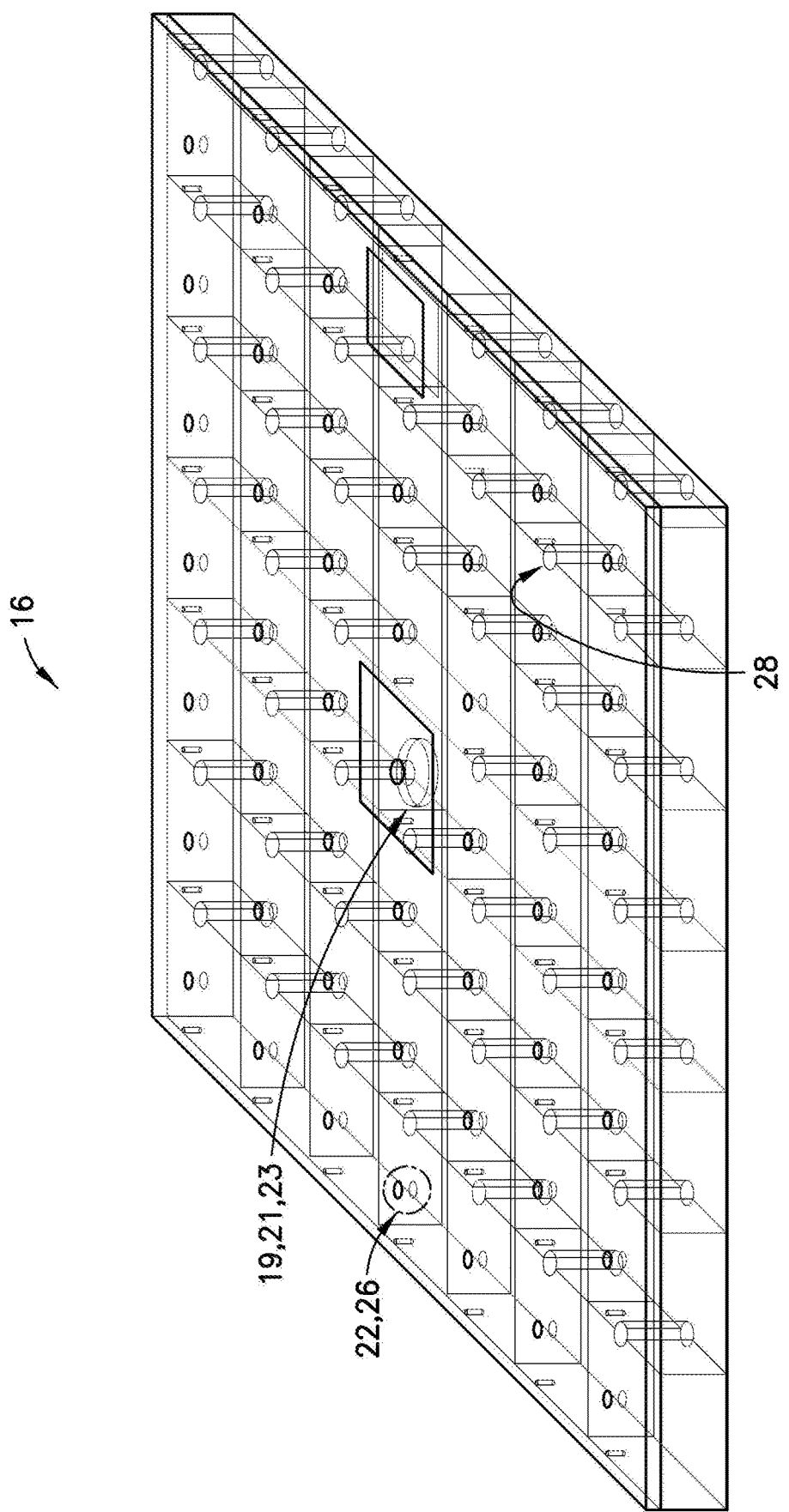
FIG. 9 shows a perspective phantom view of the top and bottom portions of the cartridge lid shown in FIG. 8 assembled.
Figure 10:
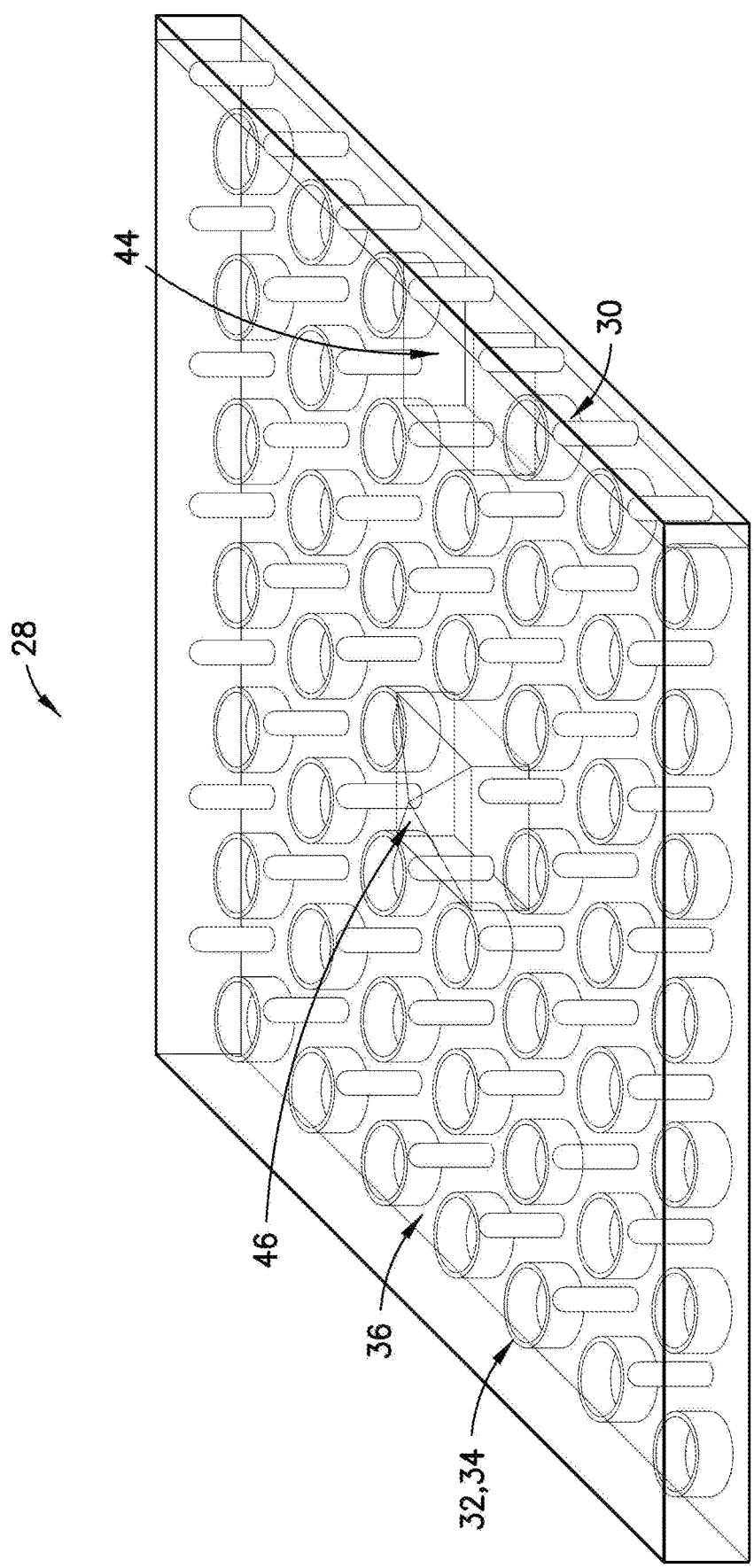
FIG. 10 shows a perspective view of the entire cartridge tray shown in FIG. 3.
Figure 11:
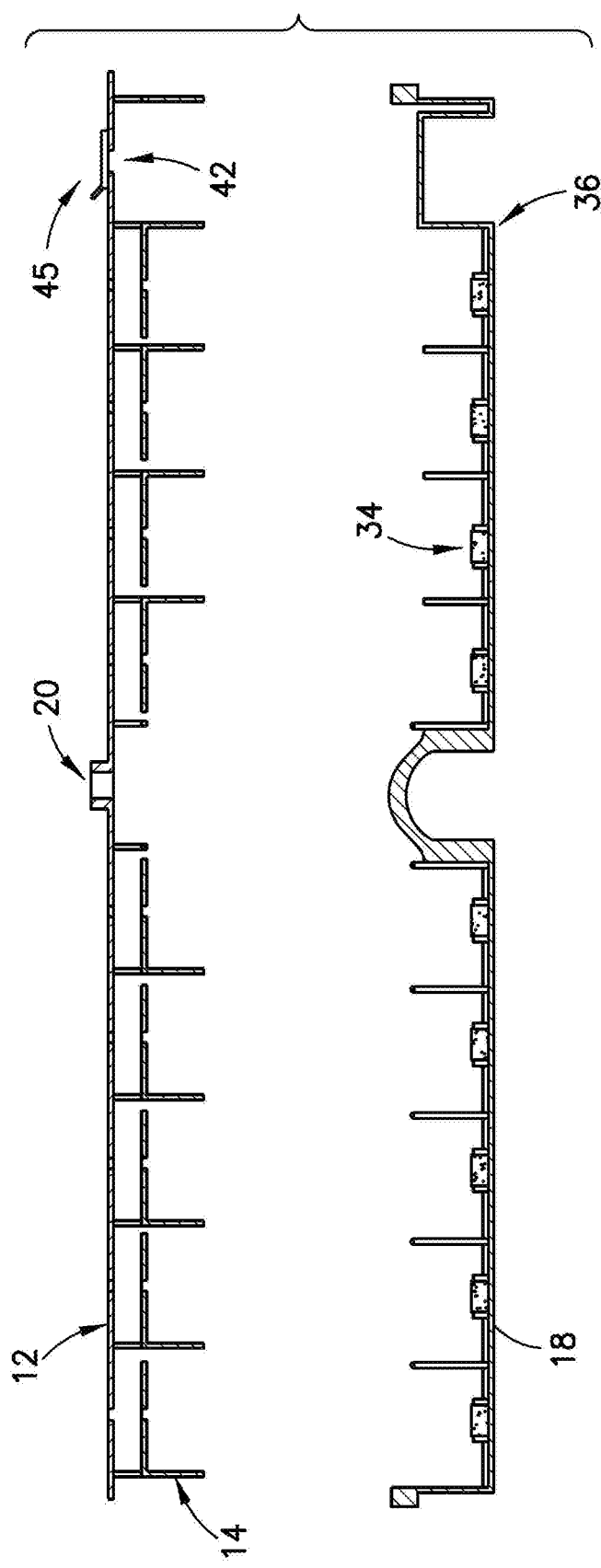
FIG. 11 shows a side plan view of the cartridge lid assembly and cartridge tray shown in FIG. 8 prior to assembly.

Referring to FIGS. 6 and 7, the top lid portion 12 and bottom lid portion 14 also include snap post apertures 38 and snap posts 40, respectively, to allow the top lid portion 12 to snap into the bottom lid portion 14 to form the cartridge lid assembly 16, as illustrated in FIG. 2.

As noted previously, once the cartridge lid assembly is positioned onto the cartridge tray 18 in the second position, a grid of segregated compartments 24 is formed. Vents 28 and pressure escaping outlet 42 maintain desired compartment conditions during the sample injection process and "push-down" action of the cartridge lid assembly 16 onto the cartridge tray 18. Vents 28 allow the pressure among the compartments to equilibrate. Pressure escaping outlet 42 is configured to allow the bacterial detection cartridge 10 to vent if pressure builds up above a predetermined threshold.

Figure 16B:
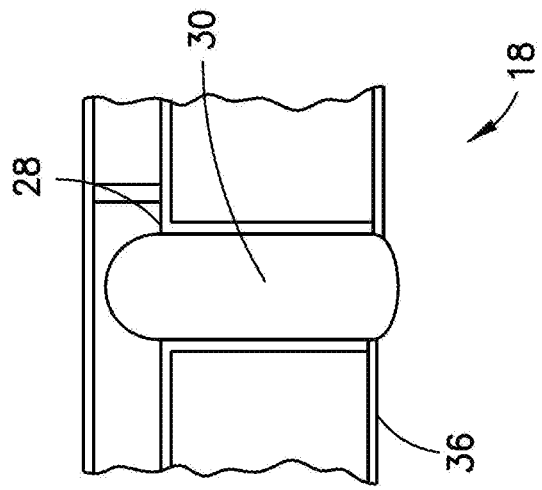
FIGS. 16A-B show air escaping the cartridge tray during the transition from the first position to the second position.
Figure 16A:
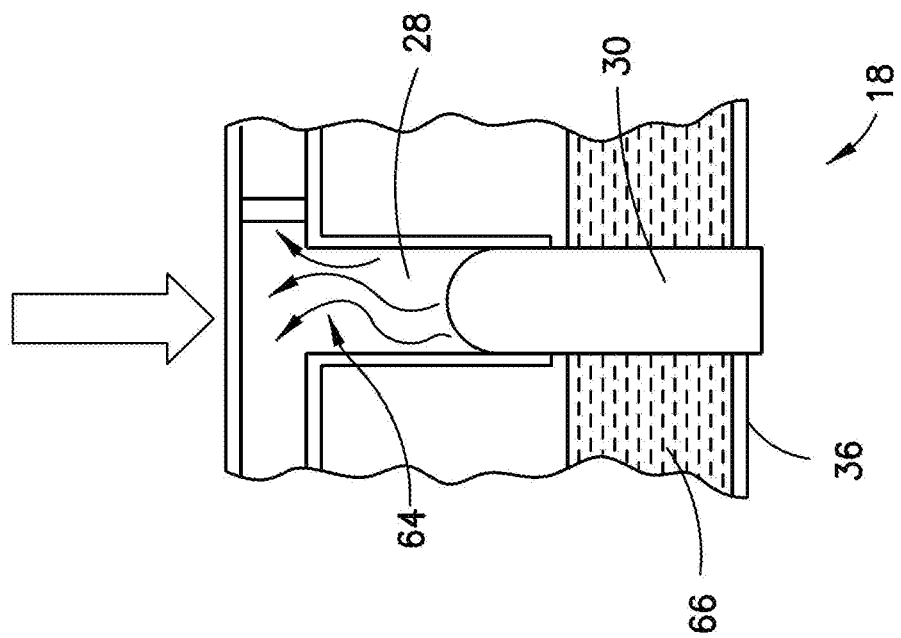
Figure 17:
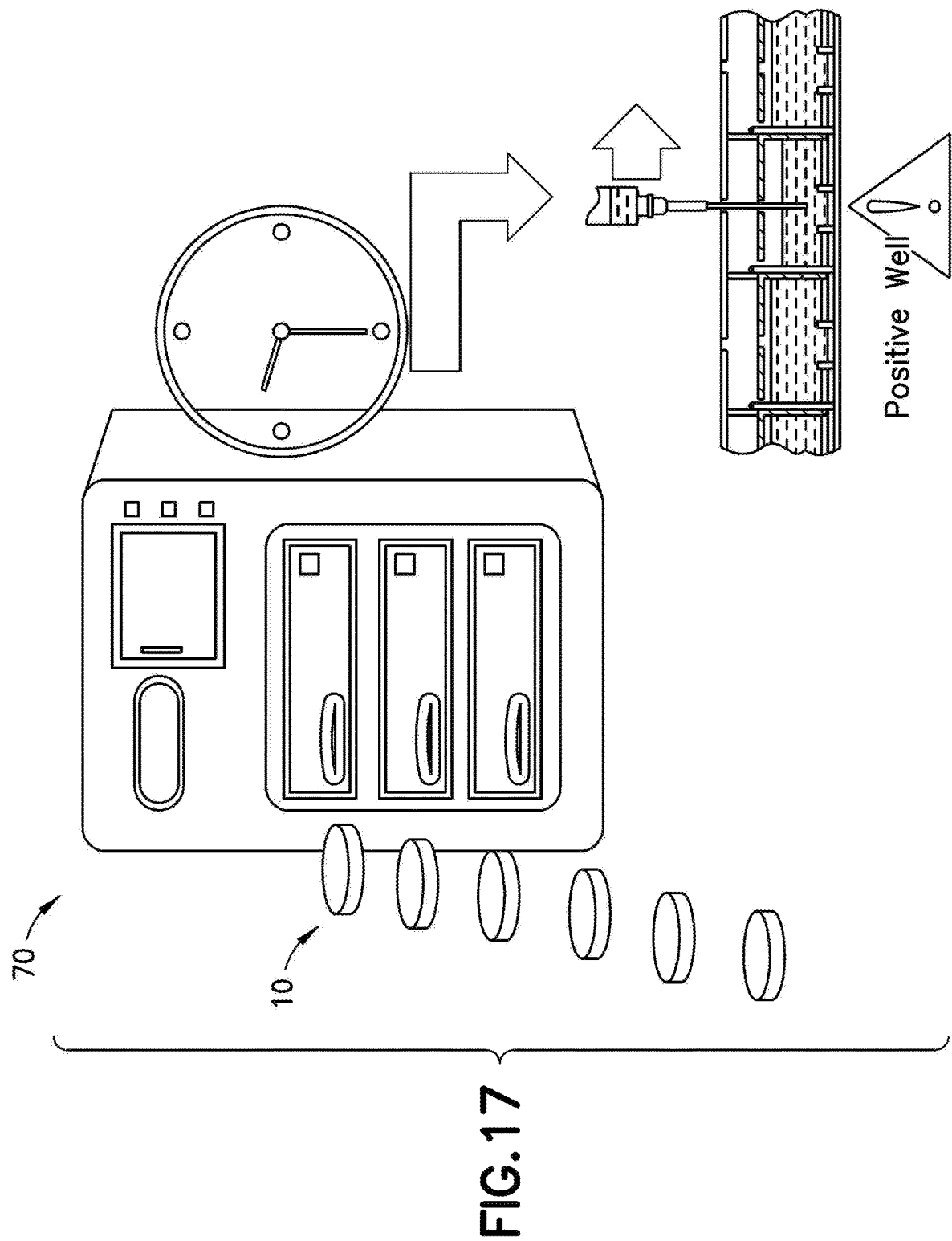
FIG. 17 shows a schematic view of the cartridge undergoing bacterial detection.

The seal rods 30 on the cartridge tray 18 are located such that each compartment 24 is adjacent to at least one seal rod 30. The seal rod 30 in each compartment 24 aligns with the vent 28 of the bottom lid portion 14. The seal rod 30 has a diameter that permits the seal rod 30 to fit within the vent 28. The length of the seal rod 30 is such that, when the cartridge lid assembly 16 is in the second position, the seal rod 30 on the cartridge tray 18 seals the vent 28. This is illustrated in FIGS. 16A-B. The pressure escaping outlet 42 on the top lid portion 12 is kept open during sample injection and push-down operation. Note that pressure escaping outlet 42 in top lid portion 12 overlies opening 43 in bottom lid portion 14 to permit pressure release through the bottom lid portion 14. Pressure escaping outlet 42 is then re-sealed for incubation of the loaded bacterial detection cartridge 10. This may be accomplished, for example, with the use of a re-sealable foil 45.

Referring generally to FIGS. 6-10, various aspects of the bacterial detection cartridge 10 in accordance with an embodiment of the invention are illustrated including top lid portion 12, bottom lid portion 14, of the cartridge lid assembly 16, and cartridge tray 18.

As illustrated in FIGS. 6-9, the sample injection port 20 comprises a sample injection aperture 19 in the top lid portion 12 that aligns with a septum 21. The septum 21 sits in a septum compartment 23 formed in the bottom lid portion 14.

Other features illustrated in FIGS. 6-10 that are not illustrated in FIGS. 1-5 include the pressure escaping outlet previously described, raised block 44, and raised inlet sample distributor 46. As described above, the pressure escaping outlet 42 allows for pressure equalization during sample introduction and as the cartridge lid assembly 16 is moved from the first position to the second position. The bottom lid portion 14 also contains an open portion 43 that aligns with the pressure escaping outlet 42 in the top lid portion 12 to allow for pressure to escape from the bacterial detection cartridge 10 through pressure outlet 42. The pressure escaping outlet 42, 43 is kept open as the cartridge lid assembly 16 is pushed down into the first and second positions on the cartridge tray 18. Once in the second position, the pressure escaping outlet 42 is re-sealed. The raised block 44 aligns with the pressure escaping outlets 42, 43. The raised block 44 prevents sample from flowing into the area occupied by the raised block. If there were sample 66, resin gel 34 and sensor 36 in a compartment 24 instead of the raised block 44, the entire sample 66 in the compartment 24 beneath the pressure escaping outlet 42, 43 would be exposed to the entire headspace between the top lid portion 12 and bottom lid portion 14 because of open portion 43. This headspace could hinder bacterial detection, so the raised block 44 is preferred.

The cartridge tray 18 also contains a raised inlet sample distributor 46. The raised inlet sample distributor 46 is in fluid communication with the sample injection port 20. As sample 66 is introduced by a syringe or other device, the sample 66 flows across the surface of the inlet sample distributor 46 in all directions into the cartridge tray 18. This ensures more uniform sample distribution in the cartridge assembly as it fills with sample Referring generally to FIGS. 11-18, the steps by which the bacterial detection cartridge 10 according to an embodiment of the invention is assembled and filled are illustrated. The bacterial detection cartridge 10 is illustrated in side and side perspective views in these figures. The first step is to snap the top lid portion 12 into the bottom lid portion 14 to form the cartridge lid assembly 16. The cartridge tray 18 is also prepared by inserting resin gel 34 into the vessels 32 of the tray cartridge and further by depositing the biosensor coating 36 on the surfaces previously described. The assembly steps may be completed by the manufacturer, rather than the end user. In such embodiments, the user begins with a pre-assembled cartridge lid 16 and cartridge tray 18. Assembly by a manufacturer is preferred as the bacterial detection cartridge 10 is preferably sterilized and in the first position when provided to a user.

Figure 12:
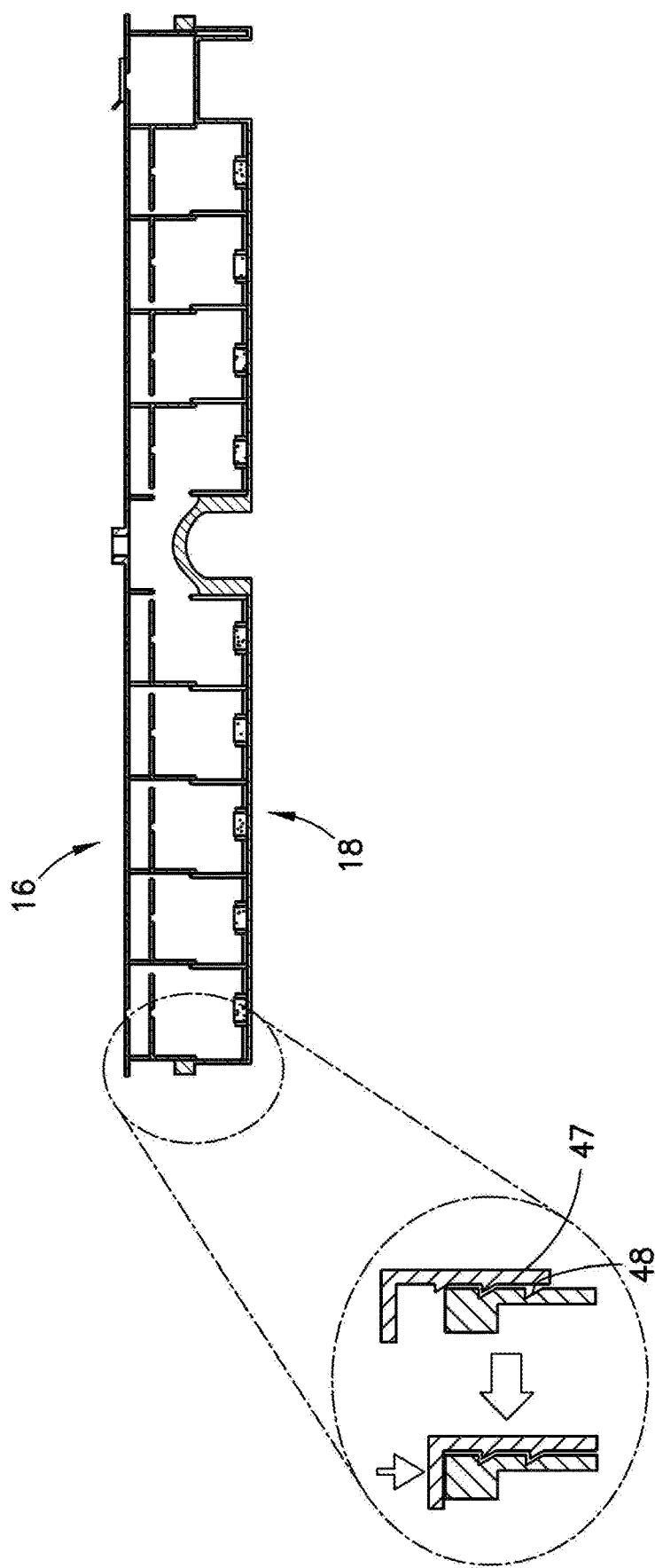
FIG. 12 shows a side plan view of the cartridge lid and cartridge tray assembled in a first position, with an enlarged view of mating features.

The user then assembles the bacterial detection cartridge 10 into its first position, as shown in FIG. 12, by pressing down the cartridge lid assembly 16 partially onto the cartridge tray 18. As mentioned above, this step is preferably performed by a manufacturer so that the components are sterilized and in the first position when provided to the user, but user assembly is still within the scope of the invention. The cartridge lid assembly 16 and cartridge tray 18 each include features to lock them together. Failure to lock indicates that the cartridge lid assembly 16 and cartridge tray are not in proper engagement. The locking features may include multiple locking features, such as protrusions and corresponding recesses, such that the cartridge lid assembly 16 and the cartridge tray 18 can lock in multiple discrete stages. Locking features may be, for example, sawteeth 47 on the cartridge lid assembly 16 and notches 48 on the cartridge tray 18. The sawteeth 47 and notches 48 are configured in the illustrated embodiment to allow the cartridge lid assembly 16 to engage and lock on the cartridge tray 18 in the first and second positions. The sawteeth 47 initially snap in to the notches 48 in the first position, after which the cartridge lid assembly 16 can be further advanced to snap the sawteeth 47 into an additional set of notches 48 to move the bacterial detection cartridge 10 into the second position.

Figure 13:
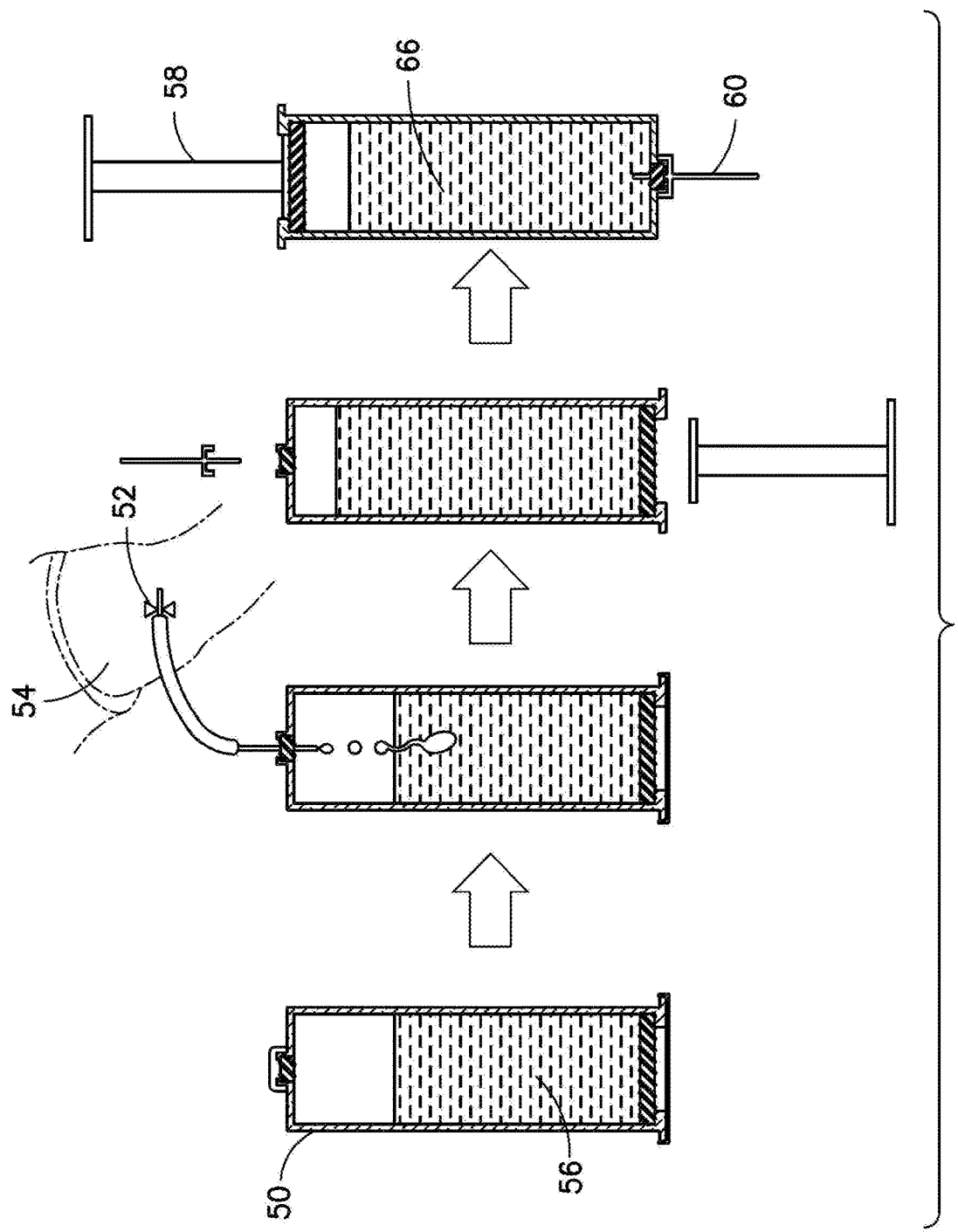
FIG. 13 shows the steps of collecting a blood sample.

Sample preparation is illustrated in FIG. 13. The sample 66 may be collected, for example, directly from the patient into syringe 50 or similar device pre-filled with growth media 56 and under a partial vacuum balanced with nitrogen or other preferred gas compositions for storage stability. In one embodiment, the syringe 50 can contain oil, described more fully below. A traditional butterfly needle 52 can be used with a first end located at the sample source in the patient 54 (e.g. in a vein) and with a second end connected to a needle in the syringe 50. A plunger 58 and needle 60 are then connected to the syringe 50 for injecting the sample 66 into the bacterial detection cartridge 10. The collection step may alternatively include multiple steps, wherein the sample is first collected from the patient, undergoes some sort of pre-processing, and is then introduced into the bacterial detection cartridge 10 via the collection tube. The sample 66 is not limited to blood, and can be any other biological sample such as spinal fluid, urine, saliva, etc.

Figure 14:
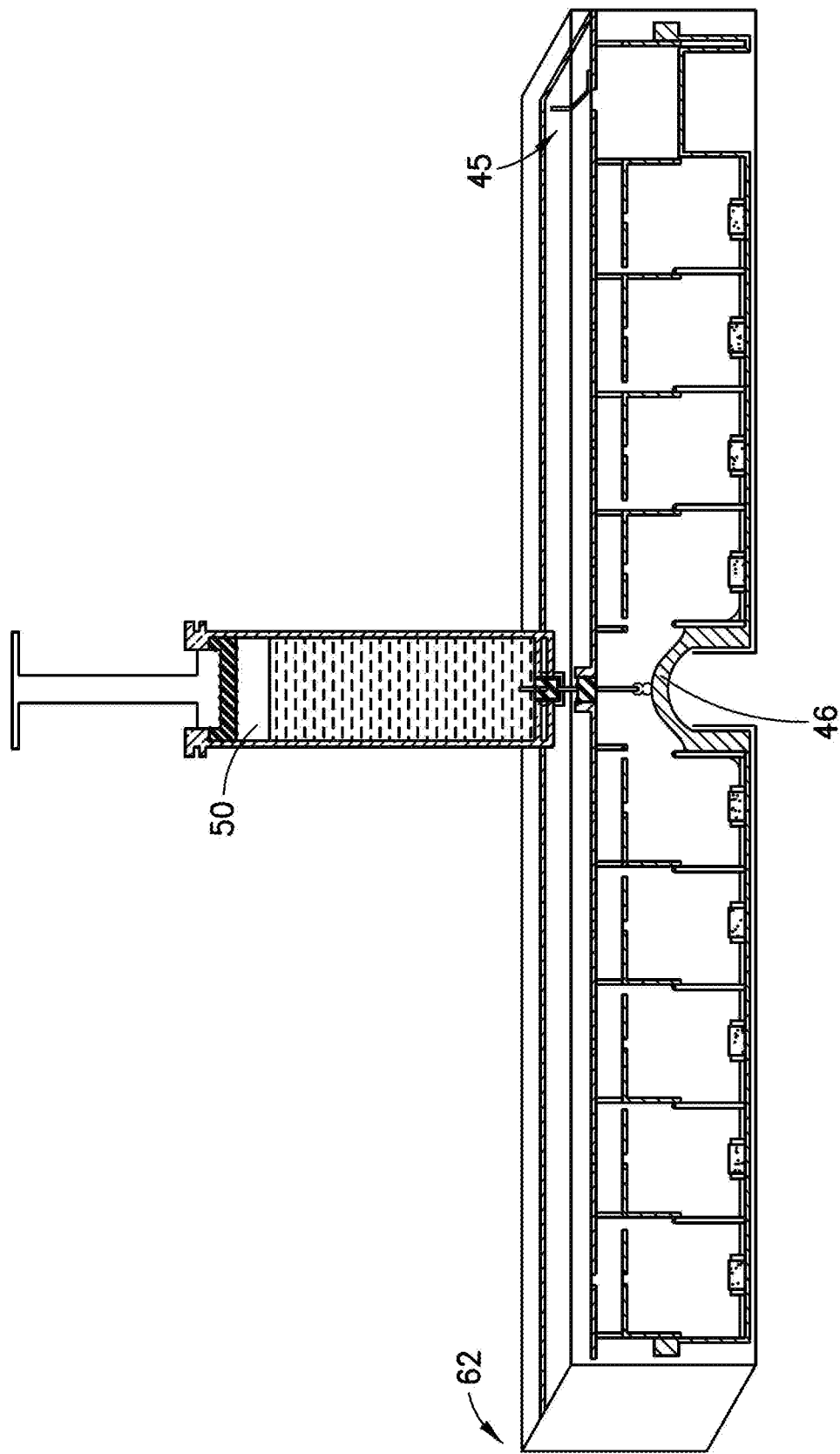
FIG. 14 shows a side view of a sample being introduced into the cartridge lid and tray in the first position.

When the bacterial detection cartridge 10 is in the first position, the spacing between the bottom lid portion 14 and the cartridge tray 18 is such that sample 66 will flow across the cartridge tray 18 and relatively uniformly fill a portion of each compartment 24 as illustrated in FIG. 15. Sample 66 will not flow into the region occupied by raised block 44. The user pierces the septum 21 in the sample injection port 20 with the needle 60 on the syringe 50, and depresses the plunger 58 to inject the sample 66 into the bacterial detection cartridge 10. Because the bacterial detection cartridge 10 is in the first position, the sample 66 can flow freely across the bottom of cartridge tray 18, with uniform distribution of sample being assisted by the raised inlet sample distribution guide 46, as shown in FIG. 14. During sample injection, the re-sealable foil 45 on the pressure escaping outlet 42 is in the open position, allowing for the pressure inside the bacterial detection cartridge 10 to equalize with the pressure outside the bacterial detection cartridge 10. A cartridge and syringe docking station 62 may optionally be employed to provide additional stability to the bacterial detection cartridge 10 and to provide a guide for the syringe 50. Automated robotic systems for providing sample to the compartments are contemplated.

After the sample 66 is fully injected and after the sample volume has equilibrated among the compartments (the skilled person would appreciate that the "self-leveling" aspect of the distribution of sample within the tray is best achieved when the tray is in a level position), the user advances the cartridge lid assembly 16 on the cartridge tray 18 until the sawteeth 47 engage the next set of notches 48, moving the bacterial detection cartridge 10 to the second position, as shown in FIG. 15. Although not specifically described herein, the assembly is easily configured to provide one or more intermediate positions.

Referring to FIGS. 16A-B, as the cartridge lid assembly 16 is advanced from the first position to the second position, the seal rods 30 advance further into the vents 28, sealing them. Before the downward projecting walls 24a-d of the compartment 24 come into contact with the sensor 36 disposed on the cartridge tray 18 surface, air 64 escapes through the vent 28. As the downward projecting walls 24a-d of the compartment advance onto the sensor 36 on the cartridge tray 18, the seal rods 30 simultaneously plug the vents 28. Once the downward projecting walls 24a-d of the compartment 24 touch the cartridge tray 18, the sample 66 is sealed into multiple compartments 24. The re-sealable foil 45 is then re-sealed to isolate the sample inside the bacterial detection cartridge 10 from the environment. If desired, gaskets in the form of tapes can be used to seal between the cartridge lid assembly 16 and cartridge tray 18 to prevent potential leaks.

Once the sample 66 is loaded into the bacterial detection cartridge 10 and sealed, the cartridge is placed into an incubator 70 to grow microorganisms in the sample. The sensor 36 detects growth, for example by detecting changes in concentration of $O_2$ and/or $CO_2$ from increased levels of bacterial metabolism, and reports each compartment 24 that tests positive for growth. As such detection techniques are well known in the art, they are not described in further detail herein. Ultrasound or similar mechanisms can be used to agitate the bacterial detection cartridge 10 during inoculation.

Figure 18:
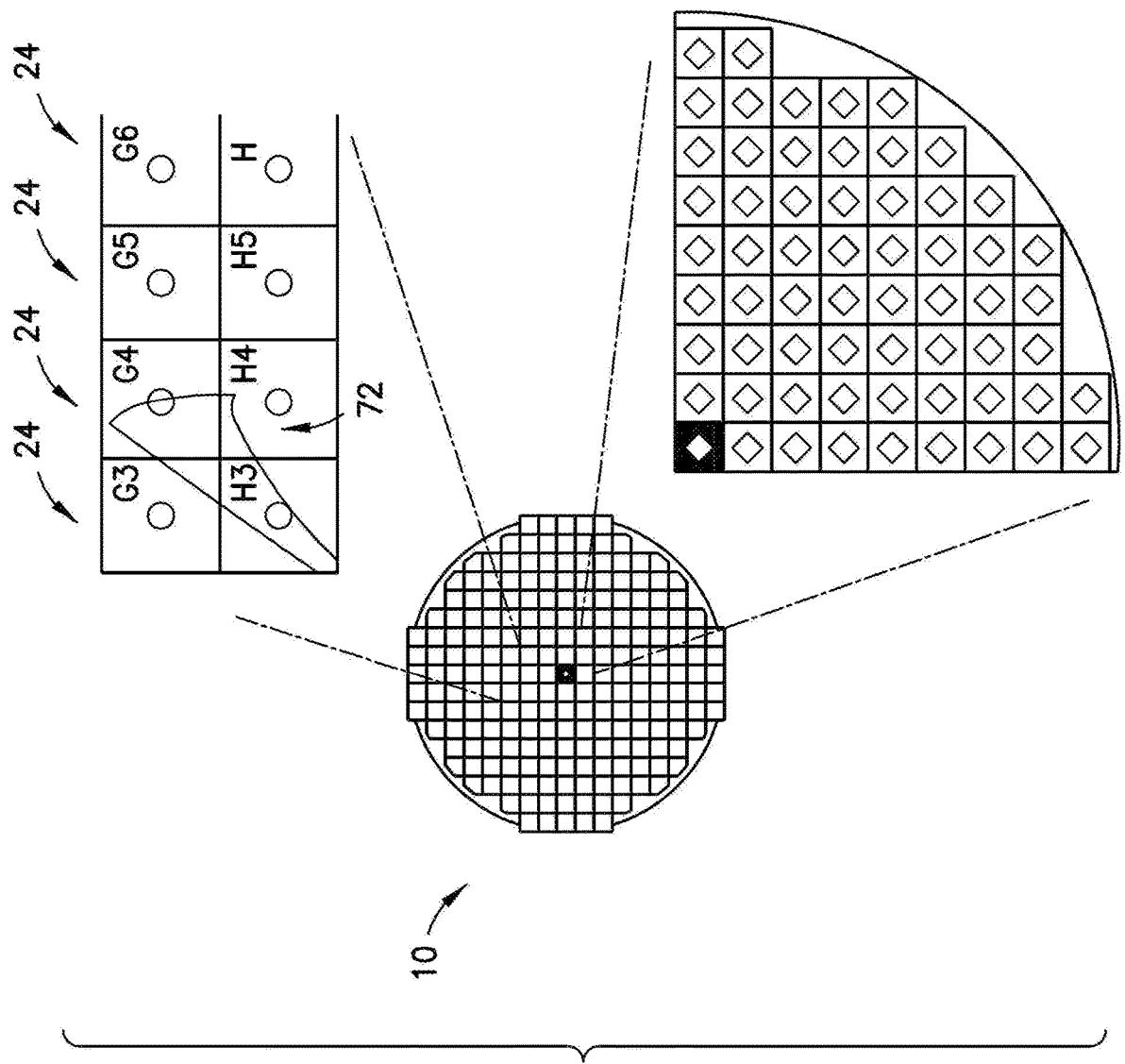
FIG. 18 shows a top plan view of an alternate embodiment of the cartridge lid assembly shown in FIG. 9 with enlarged views of individual compartments.

As shown in the embodiment illustrated in FIG. 18, the compartments 24 of the bacterial detection cartridge 10 are arranged in a grid format, with each compartment including identifiers. For example, the compartments can include a row-identifying letter and column-identifying number (G3, G4, H3, H4 etc.). Each compartment 24 that tests positive for bacterial growth by the incubator 70 is reported to the user. If any compartment 24 shows signs of bacterial growth, there is often a need for removal of the sample 66 from those compartments 24 for post-processing procedures such as identification or antibiotic susceptibility testing. The user identifies the specific compartment(s) 24 testing positive for bacterial growth, inserts a removal device such as a syringe or pipette into the desired compartment via the top and bottom lid access apertures 22, 26 respectively, piercing any adhesive foils or film 72 covering the apertures, and withdraws the positive sample 66. The user then may perform desired post-processing of the positive sample to, for example, identify the bacteria in the blood sample 66. One, some, or all of the above-mentioned steps may be automated. The bacterial detection cartridge 10 is not limited to a round dish, but can be other shapes including, but not limited to, oval or other polygons.

Figure 19:
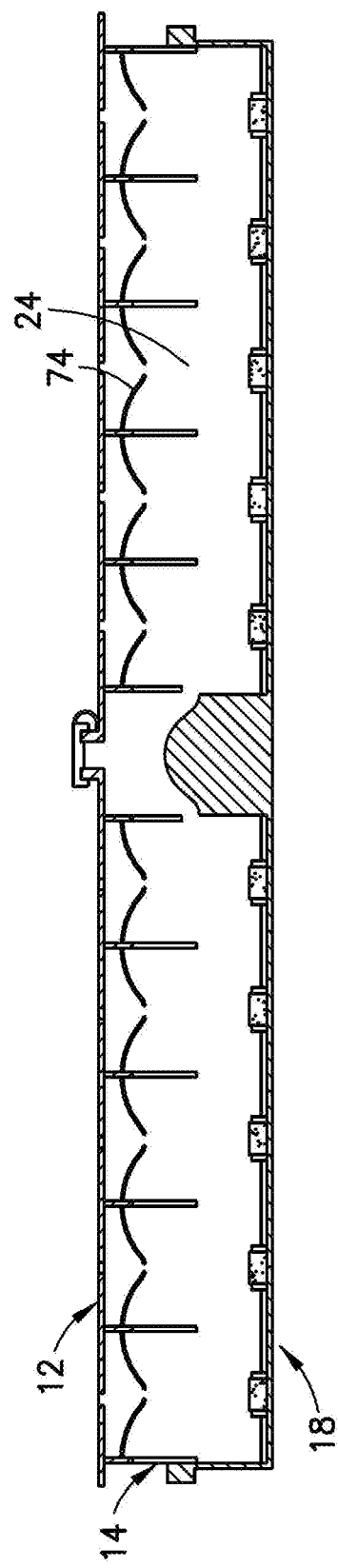
FIG. 19 shows a side plan view of an alternate embodiment of the cartridge lid and cartridge tray of FIG. 13 assembled in a first position.
Figure 20:
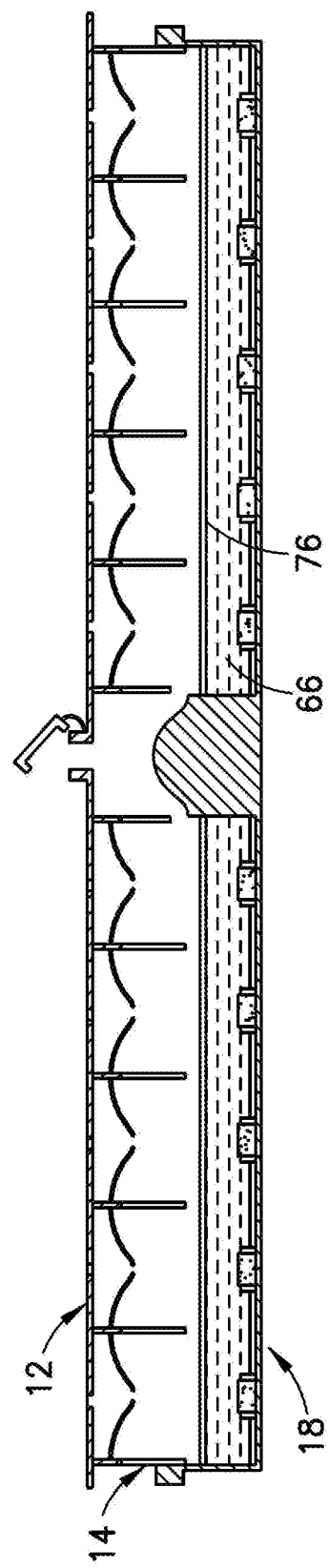
FIG. 20 shows a side plan view of the cartridge lid and cartridge tray of FIG. 20 filled with sample and oil.

An alternate embodiment of the bacterial detection cartridge 10 is shown in FIGS. 19-20. In this embodiment, the top lid portion 12 and cartridge tray 18 are substantially similar to embodiments previously described. The top of the bottom lid portion 14, in the illustrated embodiment, is downwardly deflected towards the center of each compartment 24. This downward deflection 74 provides a guiding mechanism for insertion of an access device, such as a syringe or pipette. The downward deflection 74 further provides a barrier from the sample 66 escaping if any splash-back occurs during manipulation of the bacterial detection cartridge 10. Additionally, if a portion of sample 66 sticks to the top surface of the bottom lid portion 14, for example while transporting bacterial detection cartridge 10, the downward deflection 74 provides a path for the sample to flow down into the compartment 24. This may be especially useful considering the small volumes of sample 66 in each compartment 24.

FIG. 20 shows another embodiment of the invention. Syringe 50 (FIG. 13) is prepackaged with oil, for example mineral oil, in addition to growth media 56. The sample 66 with growth media 56 and oil is loaded into the bacterial detection cartridge 10 as described above. Once loaded, the low density and low miscibility of the oil causes the oil to migrate to the upper surface of the sample 66, creating an oil layer 76. Other fluids can be used besides mineral oil, including, but not limited to, silicone oil and organic polymers. The oil layer 76 acts as a seal to isolate the sample 66 from the environment external to the oil layer 76. This fluid seal can be used alternatively, or in addition to, sealable materials such as the adhesive foils described above.

Figure 21B:
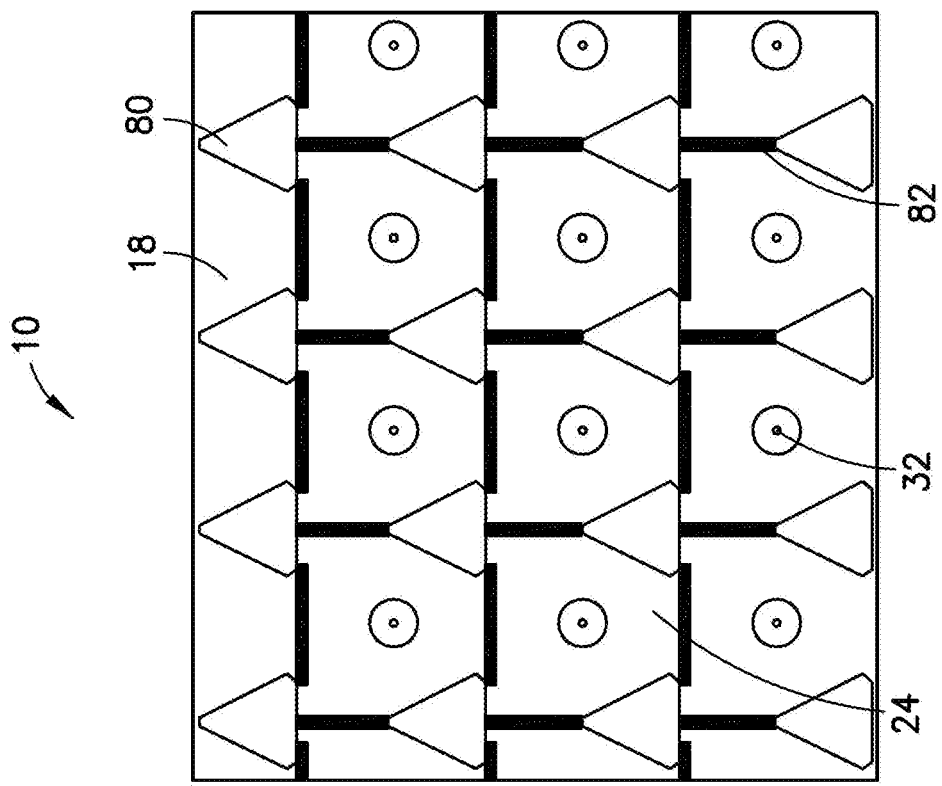
FIG. 21B shows a top plan view of the cartridge lid and tray of FIG. 21A in a second position.
Figure 21A:
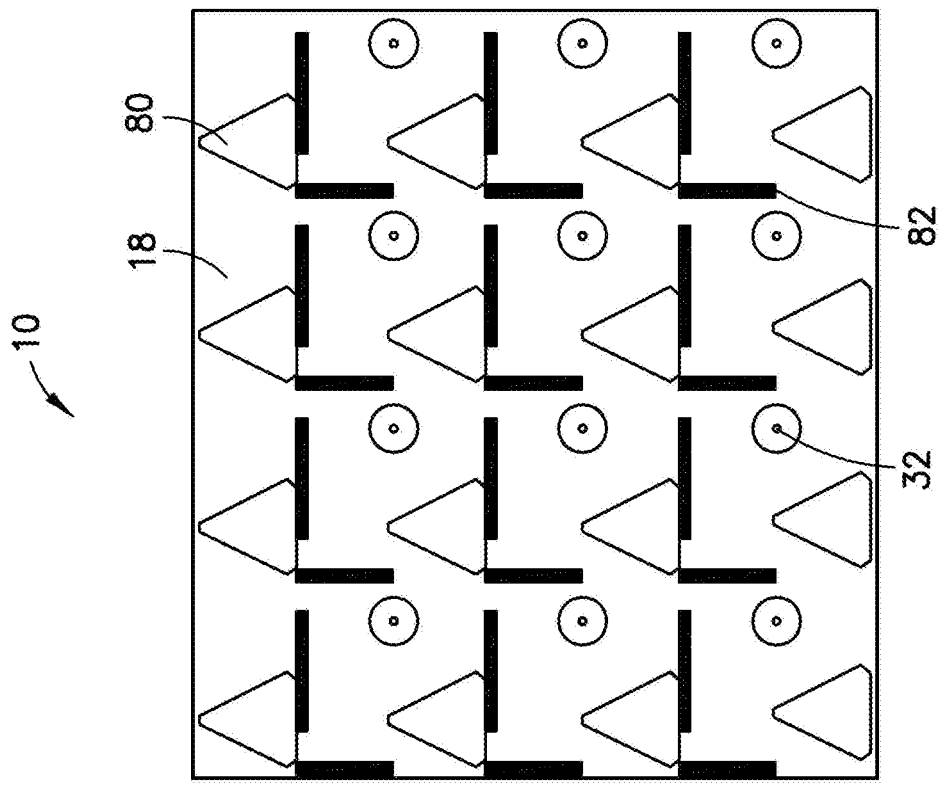
FIG. 21A shows a top plan view of an alternate embodiment of a cartridge lid and tray in a first position.
Figure 22B:
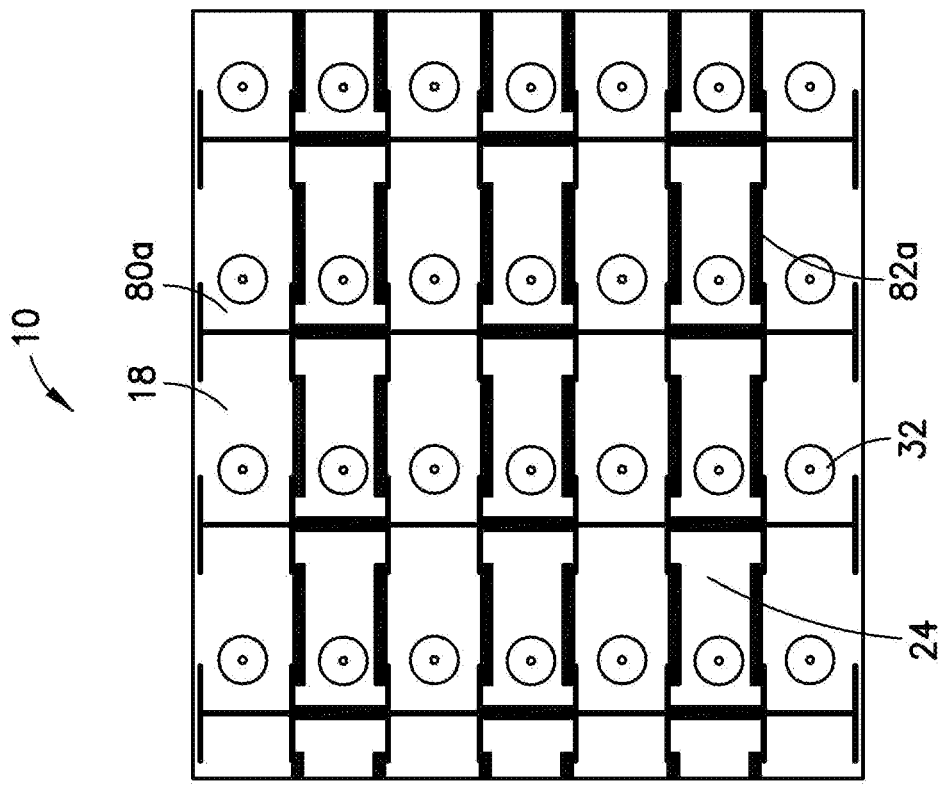
FIG. 22B shows a top plan view of an alternate embodiment of a cartridge lid and tray in a first position.
Figure 22A:
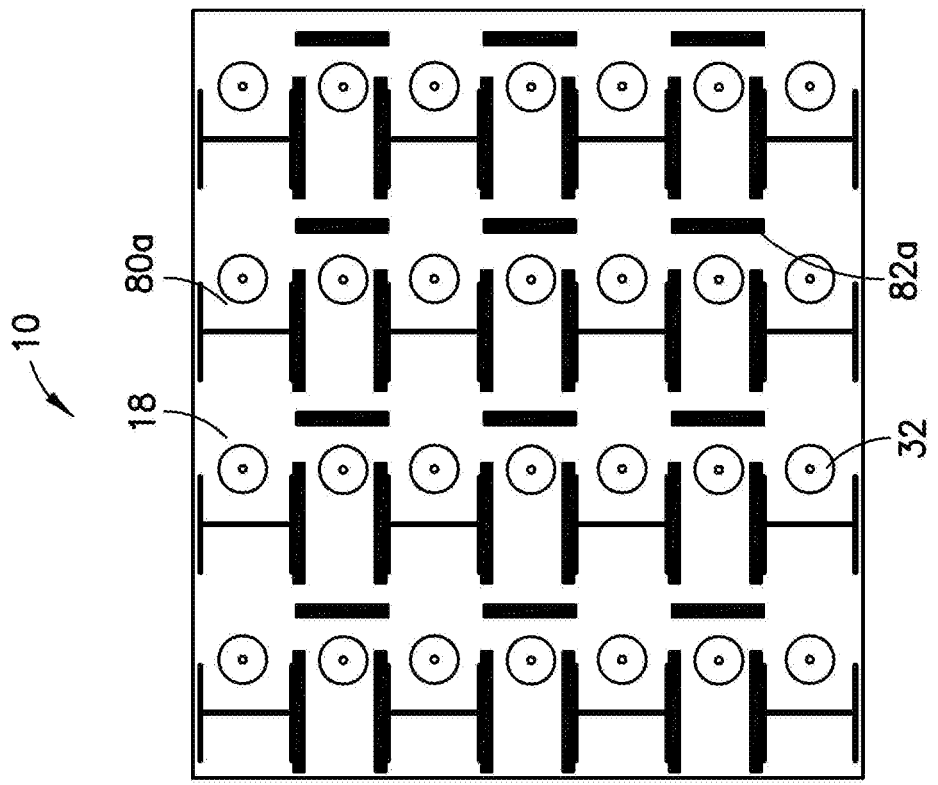
FIG. 22A shows a top plan view of an alternate embodiment of a cartridge lid and tray in a first position.

The operation of the bacterial detection cartridge 10 with two stages of pushing into a first and second position can be functionally replaced with alternate mechanisms. For example, a twist-down mechanism, or a slide-over mechanism, as shown in FIGS. 21A-B and 22A-B, can be used with a similar result. Referring to FIG. 21A, a top-down view of the bacterial detection cartridge 10 is shown. The cartridge tray 18 includes vessels 32 as described above and additionally includes posts 80. The bottom lid portion 14, in the illustrated embodiment, has downward projecting walls 82. The cartridge lid assembly 16 is placed onto the cartridge tray 18 in a first position, shown in FIG. 21A, in which the walls 82 and posts 80 do not form a completely isolated compartment 24. This is functionally similar to the first position described above, in which sample 66 may be introduced to the bacterial detection cartridge 10 and flow uniformly therethrough. Once the sample 66 has been introduced, the cartridge lid assembly 16 can be translated into a second position, illustrated in FIG. 21B. In the second position, the walls 82 and posts 18 are positioned to isolate each compartment 24, including the sample 66 therein. The specific shapes of the described components can vary, based on design choices, while accomplishing a similar result. For example, FIGS. 22A-B show yet another embodiment of the slide-over mechanism, except the posts 80a are rectangular projections instead of triangular projections as in FIGS. 21A-B. The walls 82a shown in FIGS. 22A-B are shaped to correspond to the projections 80a such that the cartridge lid assembly 16 can be slid from a first position (FIG. 22A) in which sample 66 can freely flow to a second position (FIG. 22B) in which compartments 24 isolate the sample.

Figure 23:
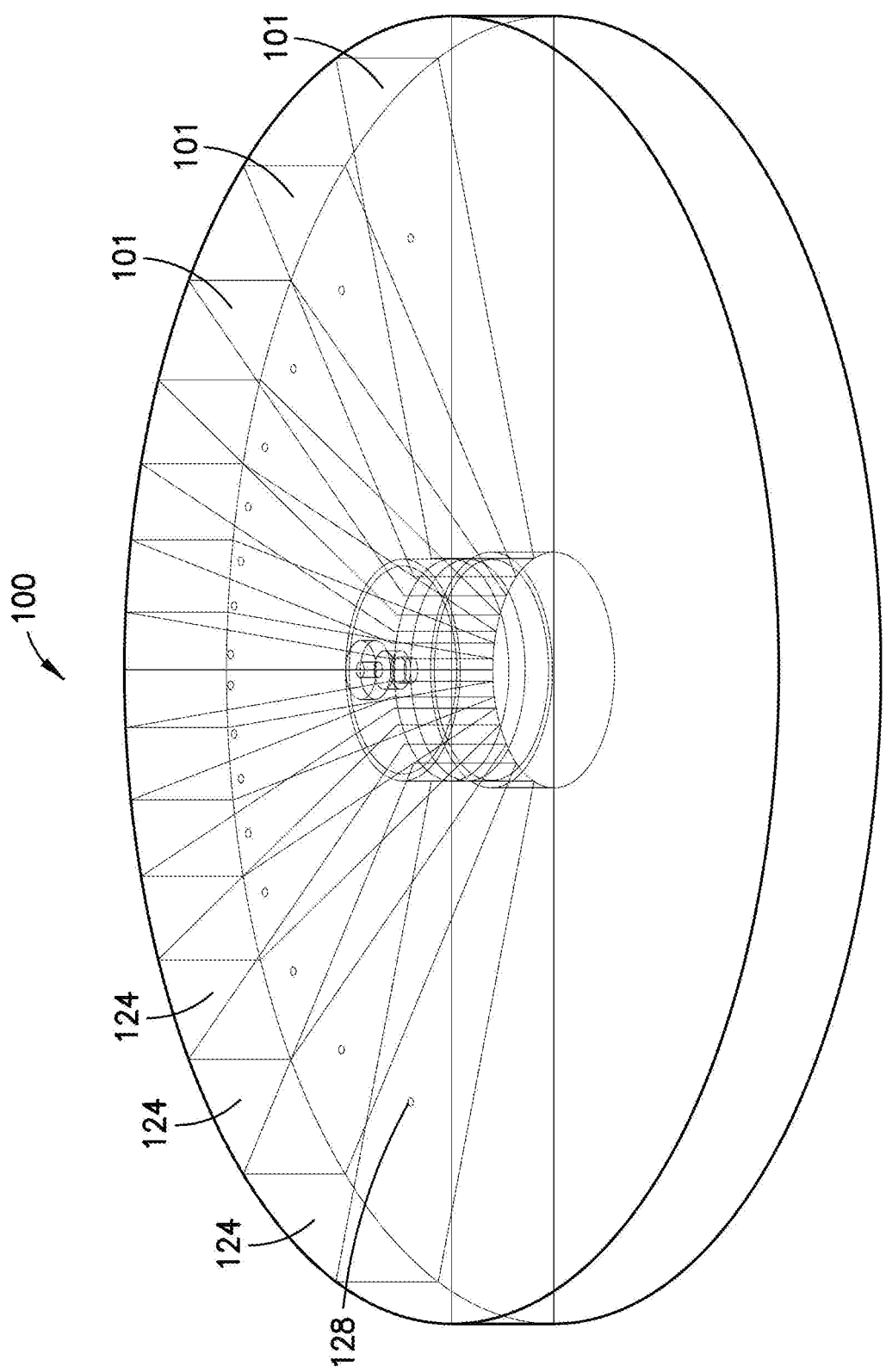
FIG. 23 shows a perspective phantom view of a bacterial detection cartridge with portions omitted according to one embodiment of the invention.

A further embodiment of a bacterial detection cartridge 100 is illustrated in FIG. 23. In this embodiment, bacterial detection cartridge 100 is a circular disk with a plurality of radially extending walls 101. A plurality of compartments 124 are created by the walls 101 in combination with the bacterial detection cartridge 100, each compartment being defined by two adjacent walls 101 and the top, bottom, and side walls of the bacterial detection cartridge. FIG. 23 illustrates a 32 compartment embodiment, with half of the compartments omitted for clarity of illustration. The top wall of each compartment 124 includes a vent aperture 128, providing a venting mechanism as discussed below. The vent apertures 128 may act additionally as access apertures for a pipette or other withdrawal tool to withdraw sample 166 from the corresponding compartment 124. Alternatively, each compartment 124 may include a separate access aperture (not illustrated) in addition to the venting apertures 128.

Figure 24:
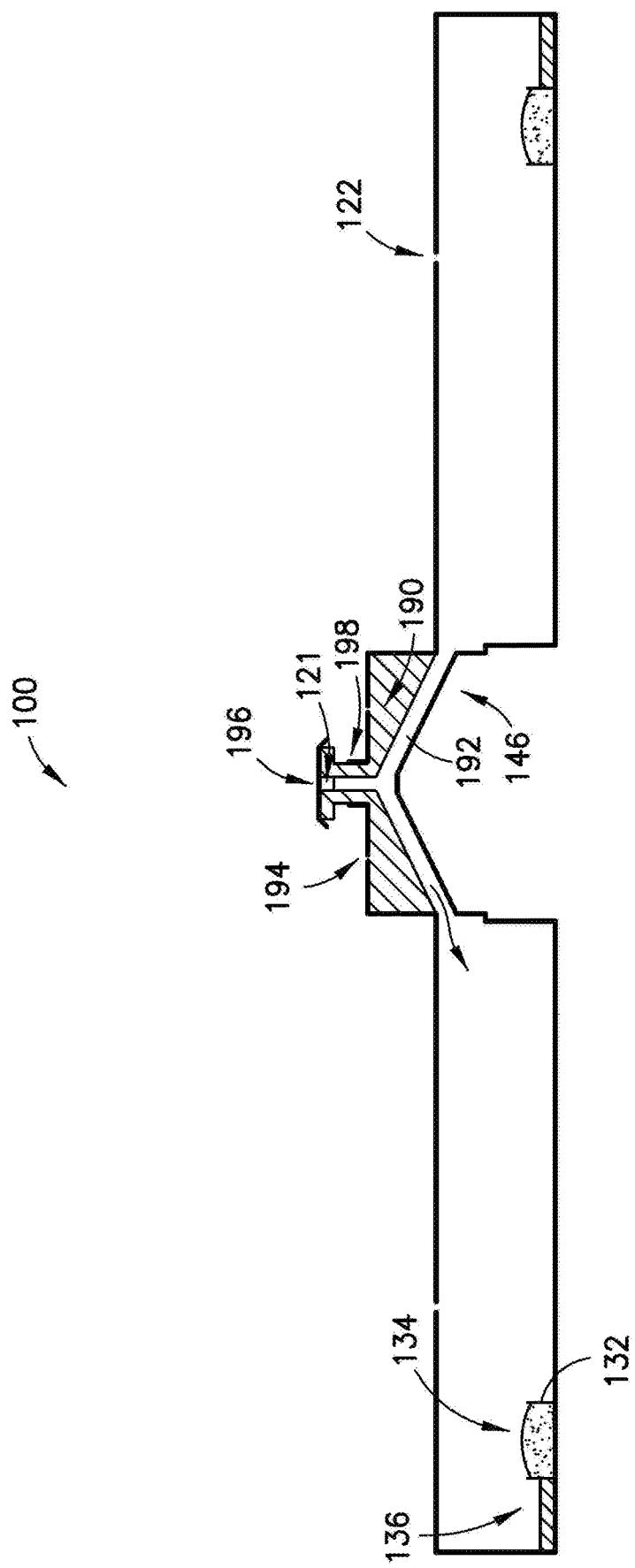
FIG. 24 shows a sectional view of the cartridge of FIG. 23 along a diameter of the cartridge.

As illustrated in FIG. 24, each compartment 124 is preloaded with biosensor coating 136 on the bottom surface. The biosensor coating 136 may be provided in an annular pattern on the bottom surface of the bacterial detection cartridge 100, or in other configurations. Although a biosensor coating 136 is preferred for the sensor, other sensors known in the art can be used without deviating from the scope of the invention. Each compartment further includes a vessel 132 configured to receive reagents such as resin gel pellets 134. In one embodiment, the vessel is a raised rim on the bottom surface of the bacterial detection cartridge 100. In other embodiments, the resin gel pellets 134 can be applied directly to the bottom surface of the bacterial detection cartridge without the use of vessels 132.

A plunger 190 is provided near the center of the bacterial detection cartridge above a raised inlet sample distributor 146. The plunger 190 has an open first position, as illustrated in FIG. 24. In the first position, the space between the plunger 190 and the raised inlet sample distributor 146 creates a flow channel 192. As sample 166 is introduced into the bacterial detection cartridge 100 when the plunger 190 is in the first position, the sample flows via the flow channel 192 into the compartments 124. The plunger 190 includes a septum 121 to facilitate introduction of sample 166.

Sample preparation is similar to that discussed with reference to FIG. 13. Once the sample 166 is prepared, it is injected, for example using syringe 150, through septum 121, flows through the flow channel 192, and fills the compartments 124, as illustrated in FIGS. 25A-B. During sample introduction, vent apertures 128 are open to allow pressure equalization.

Figure 27:
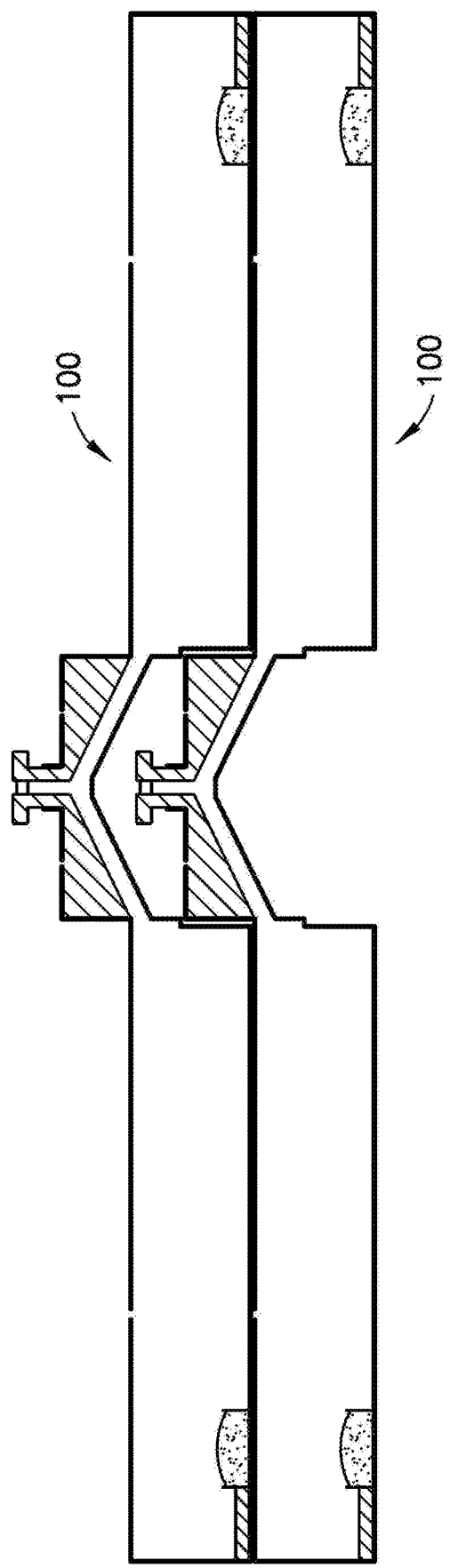
FIG. 27 shows two cartridges of the type illustrated in FIG. 24 in a stacked configuration.

Once the sample 166 has been introduced, as illustrated in FIG. 25B, the plunger 190 is moved to the closed second position, as illustrated in FIGS. 26A-B. The user presses the plunger 190 in direction D to close the plunger in the second position. The bacterial detection cartridge 100 includes snap locks 198 to lock the plunger 190 in the second position. The bacterial detection cartridge 100 includes one or more apertures 194 located above the plunger 190. These apertures 194 allow for pressure equalization to facilitate transition of the plunger 190 from the first position to the second position. Once the plunger 190 is in the second position, the flow channel 192 is sealed off, and each compartment 124 with sample 166 is sealed off to the environment with the exception of vent apertures 128. After the plunger 190 has been moved to the second position, the vent apertures 128 can be sealed, for example with a re-sealable foil 145. Similarly, the septum 121 can be sealed with, for example, a re-sealable foil 196. Once the sample 166 has been fully introduced, the plunger 190 moved to the second position, and the vent apertures 128 sealed, the bacterial detection cartridge 100 can be placed into an incubator. The growth of organisms inside the bacterial detection cartridge 100, as well as detection, removal, and processing is substantially similar to the procedures described with other embodiments above. The shape of the bacterial detection cartridge 100 allows for multiple cartridges to be stacked, as shown in FIG. 27, for easier storage and transportation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for determining the presence of a microorganism in a sample, the apparatus comprising:
   a container assembly having a top, a bottom, an inner side wall, an outer side wall, a plurality of walls extending radially from the inner side wall to the outer side wall defining a plurality of compartments, and a plunger device adapted to move from a first position to a second position,
   wherein, when in the first position, the plunger device defines a flow pathway adapted to receive a sample, the flow pathway being in fluid communication with an exterior of the container assembly and also with the plurality of compartments;
   wherein, when in the second position, the plunger device seals the flow pathway, such that the plurality of compartments are not in fluid communication with each other, and the sample in each of the plurality of compartments is isolated from the sample in other compartments.

2. The apparatus of claim 1, further comprising a plurality of sensors positioned on the bottom of the container assembly, each of the plurality of sensors being configured to detect at least one of the presence, absence or growth of a microorganism.

3. The apparatus of claim 1, further comprising a biosensor coating applied to the bottom of the container assembly, the biosensor coating being configured to detect at least one of the presence, absence or growth of a microorganism.

4. The apparatus of claim 1, further comprising a plurality of vessels projecting upwardly from the bottom of the container assembly, each one of the plurality of vessels present in a corresponding one of the plurality of compartments.

5. The apparatus of claim 4, wherein each of the plurality of vessels is at least partially filled with a resin gel.

6. An apparatus for determining the presence of a microorganism in a sample, the apparatus comprising:
- a container lid having a top surface and a plurality of walls projecting downward from the top surface;
- a container tray having a bottom surface and a plurality of posts projecting upward from the bottom surface, the container tray being adapted to receive a sample and to be assembled with the container lid in a first position and a second position;
- wherein, when in the first position, compartments defined by the top surface of the lid, the bottom surface of the container tray, the plurality of downward projecting walls, and the plurality of upward projecting posts, are open to each other thereby permitting the sample to flow from compartment to compartment within the container tray;
- wherein, when in the second position, the compartments are sealed off from each other, each sample portion being confined to its respective compartment.

7. The apparatus of claim 6, wherein each compartment is defined by the projecting walls, the upward projecting posts, the top surface of the container lid, and the bottom surface of the container tray.

* * * * *